US012559747B2

(12) United States Patent
Fletcher et al.

(10) Patent No.: US 12,559,747 B2
(45) Date of Patent: Feb. 24, 2026

(54) RETINITIS PIGMENTOSA TREATMENT

(71) Applicant: Vision Pharma PTY LTD, Mount Pleasant (AU)

(72) Inventors: Sue Fletcher, Bayswater (AU); Ianthe Pitout, Canning Vale (AU); Jayna Grainok, Perth (AU); Steve D. Wilton, Applecross (AU); Fred K. Chen, Nedlands (AU)

(73) Assignee: VISION PHARMA PTY LTD, Mount Pleasant (AU)

( * ) Notice: Subject to any disclaimer, the term of this patent is extended or adjusted under 35 U.S.C. 154(b) by 1087 days.

(21) Appl. No.: 17/614,495

(22) PCT Filed: May 25, 2020

(86) PCT No.: PCT/AU2020/050516
§ 371 (c)(1),
(2) Date: Nov. 26, 2021

(87) PCT Pub. No.: WO2020/237294
PCT Pub. Date: Dec. 3, 2020

(65) Prior Publication Data
US 2022/0298506 A1      Sep. 22, 2022

(30) Foreign Application Priority Data

May 27, 2019    (AU) ................................ 2019901804
Oct. 10, 2019    (AU) ................................ 2019903812

(51) Int. Cl.
*C12N 15/113*        (2010.01)
*A61P 27/02*          (2006.01)

(52) U.S. Cl.
CPC ............ *C12N 15/113* (2013.01); *A61P 27/02* (2018.01); *C12N 2310/11* (2013.01)

(58) Field of Classification Search
CPC .............. C12N 15/113; C12N 2310/11; C12N 2310/315; C12N 2310/3513; C12N 2320/33; C12N 15/1137; C12N 2310/314; C12N 2310/3233; C12N 2310/3145; C12N 2310/321; C12N 2310/3521; A61P 27/02; A61K 9/0019; A61K 9/0048; A61K 31/7088; A61K 31/712
See application file for complete search history.

(56) References Cited

U.S. PATENT DOCUMENTS

| | | |
|---|---|---|
| 4,458,066 A | 7/1984 | Caruthers et al. |
| 5,149,797 A | 9/1992 | Pederson et al. |
| 6,287,860 B1 | 9/2001 | Monia et al. |
| 6,965,025 B2 | 11/2005 | Gaarde et al. |
| 6,969,400 B2 | 11/2005 | Rhee et al. |
| 2004/0248833 A1 | 12/2004 | Emanuele et al. |
| 2005/0048531 A1 | 3/2005 | Mittman et al. |
| 2010/0016215 A1 | 1/2010 | Moulton et al. |

FOREIGN PATENT DOCUMENTS

| | | |
|---|---|---|
| RU | 2034835 C1 | 5/1995 |
| WO | 2012/087983 A1 | 6/2012 |

OTHER PUBLICATIONS

Mao, J., Shimada, M., Inouye, S., & Inouye, M. (1995). Gene Regulation by Antisense DNA Produced in Vivo. The Journal of Biological Chemistry. vol. 270, No. 34, Issue of Aug. 25, pp. 19684-19687. (Year: 1995).*

Resta, R., Biesecker, B. B., Bennett, R. L., Blum, S., Hahn, S. E., Strecker, M. N., & Williams, J. L. (2006). A new definition of genetic counseling: National Society of Genetic Counselors' Task Force report. Journal of Genetic Counseling, 15(2), 77-83. https://doi.org/10.1007/s10897-005-9014-3 (Year: 2006).*

Khoo, B., Roca, X., Chew, S. L., & Krainer, A. R. (2007). Antisense oligonucleotide-induced alternative splicing of the APOB mRNA generates a novel isoform of APOB. BMC Molecular Biology, 8(1), 3. https://doi.org/10.1186/1471-2199-8-3 (Year: 2007).*

Venturini, G., Rose, A. M., Shah, A. Z., Bhattacharya, S. S., & Rivolta, C. (2012). CNOT3 Is a Modifier of PRPF31 Mutations in Retinitis Pigmentosa with Incomplete Penetrance. PLoS Genetics, 8(11), e1003040. https://doi.org/10.1371/journal.pgen.1003040 (Year: 2012).*

Bechara, C., & Sagan, S. (2013). Cell-penetrating peptides: 20 years later, where do we stand? FEBS Letters, 587(12), 1693-1702. https://doi.org/10.1016/j.febslet.2013.04.031 (Year: 2013).*

Wight, M., & Werner, A. (2013). The functions of natural antisense transcripts. Essays in Biochemistry, 54, 91-101. https://doi.org/10.1042/bse0540091 (Year: 2013).*

Bacchi, N., Casarosa, S., & Denti, M. A. (2014). Splicing-Correcting Therapeutic approaches for retinal dystrophies: where endogenous gene regulation and specificity matter. Investigative Ophthalmology & Visual Science, 55(5), 3285. https://doi.org/10.1167/iovs.14-14544 (Year: 2014).*

Zhang, Q. (2016). Retinitis pigmentosa. Asia-Pacific Journal of Ophthalmology, 5(4), 265-271. https://doi.org/10.1097/apo.0000000000000227 (Year: 2016).*

Oberemok, V. V., Laikova, K. V., Repetskaya, A. I., Kenyo, I. M., . . . & Kubyshkin, A. V. (2018). A Half-Century history of applications of antisense oligonucleotides in medicine, agriculture and forestry: We should continue the journey. Molecules, 23(6), 1302. https://doi.org/10.3390/molecules23061302 (Year: 2018).*

Spinraza Prescribing Pamphlet revised Oct. 2018 (Year: 2018).*

Pitout, Ianthe (2018). Modulation of Modifiers of Pre-mRNA Splicing: A Therapeutic Strategy for Amenable Inherited Diseases. Thesis submitted at Murdoch University. (Year: 2018).*

(Continued)

*Primary Examiner* — J. E. Angell
*Assistant Examiner* — Sarah E Allen
(74) *Attorney, Agent, or Firm* — Morgan, Lewis & Bockius LLP

(57) ABSTRACT

An isolated or purified antisense oligomer for modifying pre-mRNA splicing in the CNOT3 gene transcript or part thereof.

14 Claims, 14 Drawing Sheets
Specification includes a Sequence Listing.

(56) References Cited

OTHER PUBLICATIONS

Pitout, I., "Modulation of modifiers of Pre-mRNA splicing: A therapeutic strategy for amenable inherited diseases." PhD Thesis, Murdoch University, May 2018.

Venturini, et al. "CNOT3 is a modifier of PRPF31 mutations in retinitis pigmentosa with incomplete penetrance." PLoS Genetics. Nov. 2012, vol. 8, No. 11.

Diakatou, et al. "Genome Editing as a Treatment for the Most Prevalent Causative Genes of Autosomal Dominant Retinitis Pigmentosa." International Journal of Molecular Sciences. May 2019. vol. 20, No. 10, p. 2542.

Rose, et al. "Gene of the month: PRPF31." Journal of Clinical Pathology. Sep. 2017. vol. 70, No. 9, pp. 729-732. Epub Jun. 29, 2017.

Utz, et al. "Autosomal dominant retinitis pigmentosa secondary to pre-mRNA splicing-factor gene PRPF31 (RP11): review of disease mechanism and report of a family with a novel 3-base pair insertion." Ophthalmic Genetics. Dec. 2013. vol. 34, No. 4, pp. 83-88. Epub Jan. 23, 2013.

McNally, E. M., & Wyatt E. J. "Welcome to the splice age: antisense oligonucleotide-mediated exon skipping gains wider applicability." Journal of Clinical Investigation. Apr. 2016. vol. 126, No. 4, pp. 1236-1238. Epub Mar. 21, 2016.

Aartsma-Rus, & Van Ommen, G. J. "Antisense-mediated exon skipping: a versatile tool with therapeutic and research applications." RNA. Oct. 2007. vol. 13, No. 10, pp. 1609-1624. doi: 10.1261/rna.653607. Epub Aug. 7, 2007.

Miyada, C. G. and Wallace R. B. "Oligonucleotide hybridization techniques." Methods In Enzymology. vol. 154, 1987, pp. 94-107, ISSN 0076-6879, ISBN 9780121820558, https://doi.org/10.1016/0076-6879(87)54072-1. (https://www.sciencedirect.com/science/article/pii/0076687987540721).

Deveraux, et al. "A comprehensive set of sequence analysis programs for the VAX." Nucleic Acids Research. Jan. 1984. vol. 11, No. 12(1 Pt 1), pp. 387-395.

Summerton, J., & Weller, D. "Morpholino antisense oligomers: design, preparation, and properties." Antisense and Nucleic Acid Drug Development. Jun. 1997. vol. 7, No. 3, pp. 187-195. doi: 10.1089/oli.1.1997.7.187.

Jearawiriyapaisarn, et al. "Sustained dystrophin expression induced by peptide-conjugated morpholino oligomers in the muscles of mdx mice." Molecular Therapy. Sep. 2008. vol. 16, No. 9, pp. 1624-1629. Epub Jun. 10, 2008.

Beaucage, et al. "Deoxynucleoside phosphoramidites—A new class of key intermediates for deoxypolynucleotide synthesis" Tetrahedron Letters, vol. 22, No. 20, pp. 1859-1862, 1981.

Mann et al. "Antisense-induced exon skipping and synthesis of dystrophin in the mdx mouse." PNAS. Jan. 2001. vol. 98, No. 1, pp. 42-47.

Gebski, et al. "Morpholino antisense oligonucleotide induced dystrophin exon 23 skipping in mdx mouse muscle." Human Molecular Genetics. Aug. 2003. vol. 12, No. 15, pp. 1801-1811.

Fraley, et al. "New generation liposomes: the engineering of an efficient vehicle for intracellular delivery of nucleic acids" Trends in Biochemical Sciences. 1981. vol. 6, pp. 77-80.

Mannino, R. J., & Gould-Fogerite, S. "Liposome mediated gene transfer." Biotechniques. Jul.-Aug. 1988. vol. 6, No. 7, pp. 682-690. Abstract only.

Dokka, S., & Rojanasakul, Y. "Novel non-endocytic delivery of antisense oligonucleotides." Advanced Drug Delivery Reviews. Oct. 2000. vol. 44, No. 1, pp. 35-49.

Bacchi, et al. "Splicing-correcting therapeutic approaches for retinal dystrophies: where endogenous gene regulation and specificity matter." Investigative Ophthalmology & Visual Science. May 2014. vol. 55, No. 5, pp. 3285-3294.

Friedmann, T. Progress toward human gene therapy.: Science. Jun. 1989. vol. 16, No. 244(4910), pp. 1275-1281.

Rosenerg, S. A. "Immunotherapy and gene therapy of cancer." Cancer Research. Sep. 1991. vol. 51(18 Suppl), pp. 5074s-5079s. Abstract only.

Rosenfeld, et al. "In vivo transfer of the human cystic fibrosis transmembrane conductance regulator gene to the airway epithelium." Cell. Jan. 2002. vol. 68, No. 1, pp. 143-155.

Rosenfeld, et al. "Adenovirus-mediated transfer of a recombinant alpha 1-antitrypsin gene to the lung epithelium in vivo." Science. Apr. 1991. vol. 252, No. 5004, pp. 431-434.

Brigham, et al. "In vivo transfection of murine lungs with a functioning prokaryotic gene using a liposome vehicle." American Journal of Medical Sciences. Oct. 1989. vol. 298, No. 4, pp. 278-281.

Nabel, et al. "Recombinant fibroblast growth factor-1 promotes intimal hyperplasia and angiogenesis in arteries in vivo." Nature. Apr. 1993. vol. 362, No. 6423, pp. 844-846.

Hazinski, et al. "Localization and induced expression of fusion genes in the rat lung." American Journal of Respiratory Cell and Molecular Biology. Mar. 1991. vol. 4, No. 3, pp. 206-209.

Wang, C. Y., & Huang, L. "pH-sensitive immunoliposomes mediate target-cell-specific delivery and controlled expression of a foreign gene in mouse." PNAS. Nov. 1987. vol. 84, No. 22, pp. 7851-7855.

Wu, G. Y., & Wu, C. H. "Receptor-mediated gene delivery and expression in vivo." Journal of Biological Chemistry. Oct. 1988. vol. 263, No. 29, pp. 14621-14624.

Wolff, et al. "Direct gene transfer into mouse muscle in vivo." Science. Mar. 1990. vol. 247(4949 Pt 1), pp. 1465-1468.

Anderson, W. F. "Human gene therapy." Science. May 1992. vol. 256, No. 5058, pp. 808-813.

Barteau, et al. "Physicochemical parameters of non-viral vectors that govern transfection efficiency." Current Gene Therapy. Oct. 2008. vol. 8, No. 5, pp. 313-323.

Mueller, et al. "Gene therapy for cystic fibrosis." Clinical Reviews in Allergy Immunology. Dec. 2008. vol. 35, No. 3, pp. 164-178.

Li, S-D., & Huang, L. "Gene therapy progress and prospects: non-viral gene therapy by systemic delivery." Gene Therapy. Sep. 2006. vol. 13, No. 18, pp. 1313-1319.

Simoes, et al. "Cationic liposomes for gene delivery." Expert Opinion on Drug Delivery. Mar. 2005. vol. 2, No. 2, pp. 237-254.

Mann, et al. "Improved antisense oligonucleotide induced exon skipping in the mdx mouse model of muscular dystrophy." Journal of Gene Medicine. Nov.-Dec. 2002. vol. 4, No. 6, pp. 644-654.

Mellough, et al. "Efficient stage-specific differentiation of human pluripotent stem cells toward retinal photoreceptor cells." Stem Cells. Apr. 2012. vol. 30, No. 4, pp. 673-686.

Rose, et al. "Variant haploinsufficiency and phenotypic non-penetrance in PRPF31-associated retinitis pigmentosa" Clinical Genetics. Aug. 2016. vol. 90, No. 2, pp. 118-126. doi: 10.1111/cge. 12758. Epub Mar. 4, 2016.

Rose, et al. "Dominant PRPF31 Mutations Are Hypostatic to a Recessive CNOT3 Polymorphism in Retinitis Pigmentosa: A Novel Phenomenon of Linked Trans-Acting Epistasis" Annals of Human Genetics. Oct. 2013. vol. 78, No. 1, pp. 62-71.

International Search Report and Written Opinion issued on International Patent Application No. PCT/AU2020/050516, dated Jun. 23, 2020.

Strausberg et al., "*Homo sapiens* CCR4-NOT transcription complex, subunit 3, mRNA (cDNA clone MGC:17152 IMAGE:4181383), complete cds," GenBank Accession No. BC016474.1, 3 pp. https://www.ncbi.nlm.nih.gov/nuccore/BC016474.1.

Chi et al., "Safety and antisense oligonucleotide and siRNA-based therapeutics," Drug Discovery Today, 22 (5), 823-833 (May 2017).

Lebedeva et al., "Phosphorothioate oligodeoxynucleotides as inhibitors of gene expression: antisense and non-antisense effects," Applications of antisense therapies to restenosis, 99-117 (1999).

Mills et al., "VP-001 as an interventional therapy for patients with PRPF31 mutation-associated retinal dystrophy," PYC Therapeutics, 1 pp. (May 2023).

"Presentation of RP11 Clinical Trial Data at APVRS 2024," PYC Therapeutics APVRS, 17 pp. (Nov. 22, 2024).

"RP11 Safety Review Committee Approves Dose Escalation to Final Patient Cohort," PYC Therapeutics ASX Announcement, 3 pp. (Nov. 5, 2024).

(56)          References Cited

OTHER PUBLICATIONS

Chen et al., "The Platypus Study: a Phase 1 First-in-Human Study of VP-001, a peptide-oligonucleotide conjugate designed to treat Retinitis Pigmentosa Type 11 (RP11) due to pathogenic PRPF31 variants," PYC Therapeutics Presentation at Ranzco, 1 pp. (Oct. 31, 2024).
"Interim Update on Progress in RP11 Repeat Dose Clinical Trials," PYC Therapeutics ASX Announcement, 3 pp. (Oct. 22, 2024).
"US FDA Grants Orphan Drug Designation to PYC Drug Candidate," PYC Therapeutics ASX Announcement, 3 pp. (Oct. 21, 2024).
"E&P Healthcare Conference Presentation," PYC Therapeutics E&P Healthcare Conference, 14 pp. (Sep. 12, 2023).
"Vision Improvement in Multiple RP11 Patients," PYC Therapeutics ASX Announcement, 6 pp. (Aug. 12, 2024).
"RP11 Clinical Trial Update—Amended announcement," PYC Therapeutics ASX Announcement, 11 pp. (Aug. 5, 2024).
"RP11 Clinical Trial Update," PYC Therapeutics ASX Announcement, 9 pp (Aug. 5, 2024).
"Extension of RP11 Single Dose Study into Multiple Dose Format," PYC Therapeutics ASX Announcement, 5 pp. (Jul. 23, 2024).
"Initial Dosing Completed in Cohort 1 of RP11 Multiple Dose Trial," PYC Therapeutics ASX Announcement, 5 pp. (Jul. 17, 2024).
"Commencement of RP11 Multiple Dose Trail," PYC Therapeutics ASX Announcement, 5 pp. (Jul. 10, 2024).
"RP11 Drug Candidate Safe and Well Tolerated," PYC Therapeutics ASX Announcement, 3 pp. (Jul, 1, 2024).
"RP11 Clinical Trial Update—Dosing Completed in Patient Cohort 4," PYC Therapeutics ASX Announcement, 4 pp. (May 16, 2024).
Jackson et al., "A first-in-class therapeutic for the treatment of visual loss in Retinitis Pigmentosa Type 11 patients," PYC Therapeutics ARVO Presentation, 1 pp. (2024).
Chen, "Phase 1 First-in-Human Study of VP-001: A Peptide Conjugated Oligonucleotide for the Treatment of Retinitis Pigmentosa Type 11," ARVO 2024 Presentation, 17 pp. (May 6, 2024).
"RP11 Drug Candidate Safe and Well Tolerated—Progressing to Mid-Stage Human Trials," PYC Therapeutics ASX Announcement, 3 pp. (Apr. 29, 2024).
"RP11 Clinical Trial Update—Dosing Completed in Patient Cohort 3," PYC Therapeutics ASX Announcement, 4 pp. (Feb. 28, 2024).
"Euroz Hartleys Healthcare Conference Presentation," PYC Therapeutics, Perth, Australia, and San Francisco, California, 12 pp. (Feb. 6, 2024).
"PYC Progressing to High Dose Patient Cohort in RP11 Clinical Trial," PYC Therapeutics ASX Announcement, 3 pp. (Dec. 18, 2023).
"RP11 Clinical Trial—Completion of Dosing in Patient Cohort 2," PYC Therapeutics ASX Announcement, 3 pp. (Nov. 3, 2023).

Grainok et al., "Functional Disruption of a Disease Modifier Gene Using Antisense Oligomers: A Potential Molecular Therapy for PRPF31-associated Retinitis Pigmentosa 11," Murdoch University, 1 pp. (May 2021).
"Life-changing science, Q3 Investor Call," PYC Therapeutics, 9 pp. (Sep. 27, 2023).
"Safety Review Committee Approves Dose Escalation to Patient Cohort 2," PYC Therapeutics ASX Announcement, 3 pp. (Sep. 22, 2023).
"Retinitis Pigmentosa Type 11 Clinical Trial—Dosing Completed in Patient Cohort 1," PYC Therapeutics ASX Announcement, 2 pp. (Aug. 17, 2023).
"US "Katie" Designates PYC's Lead as a Fast Track Development Program," PYC Therapeutics ASX Announcement, 3 pp. (Aug. 2, 2023).
"Successful Toxicology Studies Pave Way for Phase 2 Clinical Trial," PYC Therapeutics ASX Announcement, 4 pp. (Jul. 18, 2023).
"US FDA Clears PYC to Commence the First Ever Human Trial in Retinitis Pigmentosa Type 11," PYC Therapeutics ASX Announcement, 2 pp. (Mar. 6, 2023).
"Successful Toxicology Studies Pave Way for Human Trials," PYC Therapeutics ASX Announcement, 3 pp. (Nov. 7, 2022).
"Exemplary PK Study Results Move RP11 Program Closer to First in Human Trials," PYC Therapeutics ASX Announcement, 3 pp. (May 10, 2022).
"PYC Completes Pre-IND Engagement with the FDA in the RP11 Program," PYC Therapeutics ASX Announcement, 2 pp. (Mar. 23, 2022).
"Successful Completion of Key Translational Milestone in Non-Human Primates," PYC Therapeutics ASX Announcement, 4 pp. (Nov. 16, 2021).
"PYC's RNA Drug Candidate is Able to Penetrate the Retina of a Large Eye Resembling That of a Human," PYC Therapeutics ASX Announcement, 3 pp. (Sep. 28, 2021).
"PYC Therapeutics Announces Commencement of Larger Animal Studies for Lead Program VP-001," PYC Therapeutics, ASX Announcement, 2 pp. (Jul. 14, 2021).
Grainok et al., "Modulation of CNOT3 expression using antisense oligomers to treat retinitis pigmentosa 11," PYC Therapeutics, 3541690, 1 pp. (May 3, 2021).
"PYC's Lead Investigational Drug, VP-001, Demonstrates Another Key Functional Improvement in Patient-Derived Models—A First for Any RP11 Treatment To-Date," PYC Therapeutics ASX Announcement, 4 pp. (Mar. 2, 2021).
"Life-changing Science," PYC Therapeutics ICR Conference Presentation, 18 pp. (Jan. 14, 2021).
"PYC's lead drug is effective in all patient derived models tested," PYC Therapeutics, ASX Announcement, 4 pp. (Oct. 7, 2020).
"Technical Presentation," PYC Therapeutics, 52 pp. (Oct. 9, 2020).
Roshandel et al., "Exploring microperimetry and autofluorescence endpoints for monitoring disease progression in PRPF31-associated retinopathy," Opthalmic Genetics, 42 (1), 14 pp. (Sep. 27, 2020).

* cited by examiner

Pedigree 0080
PRPF31
M1: c.1205 G>A

Pedigree: 0255
PRPF31
M1: c.267 delA a b b

C

SEQUENCE LISTING

```
<160> NUMBER OF SEQ ID NOS: 89

<210> SEQ ID NO 1
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 1
acucucuugg agacggacgc ugcua                                              25

<210> SEQ ID NO 2
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 2
aucuucccug cccuacagac gcacu                                              25

<210> SEQ ID NO 3
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 3
guaccuugga guuugcgcuu guccg                                              25

<210> SEQ ID NO 4
<211> LENGTH: 25
<212> TYPE: RNA
<213> ORGANISM: Artificial Sequence
```

<220> FEATURE:
<223> OTHER INFORMATION: Antisense Oligonucleotide

<400> SEQUENCE: 4
cggacaccuu cuugaggcag cgauc                                               25

<210> SEQ ID NO 5
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 5
gccaaauauc uucaaacugc uccac                                               25

<210> SEQ ID NO 6
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 6
uuggcugcau uguggagcug aggga                                               25

<210> SEQ ID NO 7
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 7
cuuuucuuuc ugguucgcgu uggcu                                               25

<210> SEQ ID NO 8
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 8
aucuccuucu uuaggucagc cucau                                               25

<210> SEQ ID NO 9
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 9
cagcccccuc acuuguagcu ucuua                                               25

<210> SEQ ID NO 10
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 10
uuuggucccu cagccgcugc agaug                                               25

-continued

```
<210> SEQ ID NO 11
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 11
cugccucuug uccuugaucu cguug                                          25

<210> SEQ ID NO 12
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 12
uugcgguugu cuauaagcug ccucu                                          25

<210> SEQ ID NO 13
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 13
cugggcuccu accgucucaa ugagc                                          25

<210> SEQ ID NO 14
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 14
acuuugaacc guuccauuug cugua                                          25

<210> SEQ ID NO 15
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 15
ggucucucgu uccacaacuu ugaac                                          25

<210> SEQ ID NO 16
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 16
ccucuuugcu guaagcuuug guuuu                                          25

<210> SEQ ID NO 17
<211> LENGTH: 25
<212> TYPE: RNA
<213> ORGANISM: Artificial Sequence
<220> FEATURE:
<223> OTHER INFORMATION: Antisense Oligonucleotide
```

-continued

<400> SEQUENCE: 17
accucuuccu ucuccuucug ggcag                                    25

<210> SEQ ID NO 18
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 18
cccaacucac cgugagccac uggcc                                    25

<210> SEQ ID NO 19
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 19
ugagcguguc gaugguauuc uaggg                                    25

<210> SEQ ID NO 20
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 20
caaacugguc caccugcaug uugag                                    25

<210> SEQ ID NO 21
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 21
cccuucuucu ugcgugucug cacug                                    25

<210> SEQ ID NO 22
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 22
ccucacucac auccuugucg cccuu                                    25

<210> SEQ ID NO 23
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 23
ccgcttcaag ccctcgccca gggcc                                    25

<210> SEQ ID NO 24

```
<211> LENGTH: 24
<212> TYPE: RNA
<213> ORGANISM: Artificial Sequence
<220> FEATURE:
<223> OTHER INFORMATION: Antisense Oligonucleotide

<400> SEQUENCE: 24
gugguagcgg ugcuucucga ugug                                          24

<210> SEQ ID NO 25
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 25
uggucucuag caugcgcacg uggua                                         25

<210> SEQ ID NO 26
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 26
ggcgucaacg aggauggagu cauug                                         25

<210> SEQ ID NO 27
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 27
cuccucgaag ucgggguccu gggau                                         25

<210> SEQ ID NO 28
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 28
guggcgacca gcgccugugc ugugg                                         25

<210> SEQ ID NO 29
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 29
cucauccucc auguggcugu ggcug                                         25

<210> SEQ ID NO 30
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 30
```

-continued

```
gggcgugcug cuggacuggu ugaag                                          25

<210> SEQ ID NO 31
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 31
ggcugggcug ggcgggaugg gagag                                          25

<210> SEQ ID NO 32
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 32
gugcugcugg acugguugaa gaucu                                          25

<210> SEQ ID NO 33
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 33
aucuucagag uuuuccugag guagg                                          25

<210> SEQ ID NO 34
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 34
cuguggaacg uccccucuuc uuauc                                          25

<210> SEQ ID NO 35
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 35
ucacacccac cuggcugacu ucacu                                          25

<210> SEQ ID NO 36
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 36
aggugggcgg cacagcuggg gacug                                          25

<210> SEQ ID NO 37
<211> LENGTH: 25
<212> TYPE: RNA
```

```
<213> ORGANISM: Artificial Sequence
<220> FEATURE:
<223> OTHER INFORMATION: Antisense Oligonucleotide

<400> SEQUENCE: 37 gaggggguagg ugggcggcac agcug                                          25

<210> SEQ ID NO 38
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 38
gcagcaggcg gggggccgga ggggu                                           25

<210> SEQ ID NO 39
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 39
ccguuuuugg cuggagacug cgggu                                           25

<210> SEQ ID NO 40
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 40
guggcuggga gcuggacugg ccuug                                           25

<210> SEQ ID NO 41
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 41
cugucugcca caacugagcu guaac                                           25

<210> SEQ ID NO 42
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 42
ggguuguggg ggccggaagg ggggc                                           25

<210> SEQ ID NO 43
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 43
acucacgagg ugcugggagg ugggu                                           25
```

```
<210> SEQ ID NO 44
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 44
ugccgcacug gguuccuucc uggag                                         25

<210> SEQ ID NO 45
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 45
uguucccuga gccuggggcc acgcc                                         25

<210> SEQ ID NO 46
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 46
gaggauucac aggcaguggc accag                                         25

<210> SEQ ID NO 47
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 47
cucagaggcu caggggccug gggag                                         25

<210> SEQ ID NO 48
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 48
aggguccuca augccagagc ugaug                                         25

<210> SEQ ID NO 49
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 49
gcauguggug ccaggcggcc ucuuc                                         25

<210> SEQ ID NO 50
<211> LENGTH: 25
<212> TYPE: RNA
<213> ORGANISM: Artificial Sequence
<220> FEATURE:
```

-continued

<223> OTHER INFORMATION: Antisense Oligonucleotide

<400> SEQUENCE: 50
gaggggugag gcauguggug ccagg                                          25

<210> SEQ ID NO 51
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 51
cgaauacgcu cagagucaga ggggu                                          25

<210> SEQ ID NO 52
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 52
gcucaggaug augucugugg ggagg                                          25

<210> SEQ ID NO 53
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 53
aggugcugau guacugcuca ggaug                                          25

<210> SEQ ID NO 54
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 54
ccucugacag cugcaggggc ggcug                                          25

<210> SEQ ID NO 55
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 55
ccauggacag acacccagcg acagc                                          25

<210> SEQ ID NO 56
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 56
agagcugcuc cuuggugagg ggcac                                          25

```
<210> SEQ ID NO 57
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 57
agucagaggg gugaggcaug uggug                                         25

<210> SEQ ID NO 58
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 58
gggggaggua cugccuguga gagca                                         25

<210> SEQ ID NO 59
<211> LENGTH: 22
<212> TYPE: RNA
<213> ORGANISM: Artificial Sequence
<220> FEATURE:
<223> OTHER INFORMATION: Antisense Oligonucleotide

<400> SEQUENCE: 59
gguggcaucu ggugguggua gg                                            22

<210> SEQ ID NO 60
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 60
cuccagauag uagaagauga agaag                                         25

<210> SEQ ID NO 61
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 61
gccaugacug cuucuuuagg gccuu                                         25

<210> SEQ ID NO 62

<400> SEQUENCE: 62

000

<210> SEQ ID NO 63
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 63
gaaccacauc auguacuugg ugugg                                         25
```

```
<210> SEQ ID NO 64
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 64
auggucuugg gcuccucgug ccucu                                           25

<210> SEQ ID NO 65
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 65
cuugggcucc ucgugccucu ggaac                                           25

<210> SEQ ID NO 66
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 66
cagugauggu cuugggcucc ucgug                                           25

<210> SEQ ID NO 67
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 67
cugcucaaac ucgucaguga ugguc                                           25

<210> SEQ ID NO 68
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 68
guagauguag gugcccuggc cgggg                                           25

<210> SEQ ID NO 69
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 69
gcuggcccca cuucucguag ucaaa                                           25

<210> SEQ ID NO 70
<211> LENGTH: 25
<212> TYPE: RNA
<213> ORGANISM: Artificial Sequence
<220> FEATURE:
<223> OTHER INFORMATION: Antisense Oligonucleotide
```

-continued

```
<400> SEQUENCE: 70
ucaaagguga agccuuccuu cuucc                                           25

<210> SEQ ID NO 71
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 71
gucccggucc uccagguagc gguac                                          25

<210> SEQ ID NO 72
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 72
ggggaggugg cgaccagcgc cugug                                          25

<210> SEQ ID NO 73
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 73
uccucgugcc ucuggaacca cauca                                          25

<210> SEQ ID NO 74
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 74
gggcccucac cugcucaaac ucguc                                          25

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
gaagatggcg gacaagcgca a                                              21

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
ctggccaacc tcttccttct c                                              21

<210> SEQ ID NO 77
<211> LENGTH: 20
```

-continued

```
<212> TYPE: DNA
<213> ORGANISM: Artificial Sequence
<220> FEATURE:
<223> OTHER INFORMATION: Primer

<400> SEQUENCE: 77
ctgtcagtgc agacacgcaa                                                    20

<210> SEQ ID NO 78
<211> LENGTH: 19
<212> TYPE: DNA
<213> ORGANISM: Artificial Sequence
<220> FEATURE:
<223> OTHER INFORMATION: Primer

<400> SEQUENCE: 78
ggacaggctg gagccgttt                                                     19

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
catcctgagc agtacatcag c                                                  21

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
ctccaggtag cggtactcaa                                                    20

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
gggatagtaa gatgtttgct gag                                                23

<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
gtcccatcac ttctgaagct ttgg                                               24

<210> SEQ ID NO 83
<211> LENGTH: 22
<212> TYPE: DNA
<213> ORGANISM: Artificial Sequence
<220> FEATURE:
<223> OTHER INFORMATION: Primer

<400> SEQUENCE: 83
```

-continued

```
tcaggcgttc ggtggatcga gt                                          22

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
agtgatgctg ggcactgcgg agaa                                        24

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
acagtcagcc gcatcttctt                                             20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
aggggtctac atggcaactg                                             20

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
gacgttccac agacagtgaa g                                           21

<210> SEQ ID NO 88
<211> LENGTH: 22
<212> TYPE: DNA
<213> ORGANISM: Artificial Sequence
<220> FEATURE:
<223> OTHER INFORMATION: Primer

<400> SEQUENCE: 88
gtggtagcgg tgcttctcga tg                                          22

<210> SEQ ID NO 89
<211> LENGTH: 19
<212> TYPE: DNA
<213> ORGANISM: Artificial Sequence
<220> FEATURE:
<223> OTHER INFORMATION: Primer

<400> SEQUENCE: 89
tatattcggg actcggggg                                              19
```

RETINITIS PIGMENTOSA TREATMENT

CROSS-REFERENCE TO RELATED APPLICATIONS

This is a National Stage Entry under 35 U.S.C. 371 of International Patent Application No. PCT/AU2020/050516, filed May 25, 2020, which claims priority to AU2019901804, filed May 27, 2019 and AU 2019903812, filed Oct. 10, 2019. These applications are incorporated by reference herein.

INCORPORATION BY REFERENCE OF MATERIAL SUBMITTED IN ELECTRONIC FORM

Incorporated herein by reference in its entirety is the sequence listing submitted via EFS-Web as a text file named WRA110_SEQLIST_ST25.txt, created May 9, 2022, and having a size of 17,518 bytes.

TECHNICAL FIELD

The present invention relates to the use of antisense oligomers to treat, prevent or ameliorate the effects of retinitis pigmentosa.

BACKGROUND ART

Retinitis pigmentosa (RP) is degenerative eye disease that causes severe vision impairment due to the progressive degeneration of the rod photoreceptor cells in the retina; most cases of RP are inherited. This form of retinal dystrophy manifests initial symptoms independent of age; thus, RP diagnosis occurs anywhere from early infancy to late adulthood. RP is a rare disease that affects approximately one out of 4000 individuals (more than 1.5 million people worldwide). Of the familial RP cases, 30%-40% show autosomal-dominant genetic inheritance (Hartong et al. 2006). There is currently no treatment for RP.

RP is caused by mutations in more than 50 genes. Heterozygous mutations in the PRPF31 gene cause autosomal dominant retinitis pigmentosa (adRP). In some cases, such mutations display incomplete penetrance, wherein certain carriers develop retinal degeneration while others have no symptoms at all. Asymptomatic carriers are protected from the disease by a higher than average expression of the PRPF31 allele that is not mutated.

Expression of the PRPF31 gene is controlled by the Ccr4-Not deadenylase complex. Ccr4-Not is a nine-subunit protein complex that is a master regulator of translation and mRNA stability in eukaryotic cells. The core CCR4-Not complex consists of Ccr4p, Caf1p, five Not proteins (CNot1-CNot5), Caf40p, and Caf130p in yeast.

At the present time, AAV mediated gene replacement and CRISPR/Cas9 gene editing are being explored as therapies for retinal disease. While the coding sequence of PRPF31 is within the capacity of AAV vectors, the consequences of unregulated or over-expression of PRPF31 are unknown. In addition, it is not known if ocular viral mediated gene therapies could be re-administered, since seroconversion as a consequence of intraocular viral vector injection has been reported. Furthermore, CRISPR/Cas9 gene correction will require a different product for each family's PRPF31 mutation. In addition, both the gene replacement and gene editing approaches require subretinal injection of viral vectors to achieve adequate transfection.

There is a need to provide new treatments or preventative measures for retinitis pigmentosa; or at least the provision of methods to complement the previously known treatments.

The present invention seeks to provide an improved or alternative method for treating, preventing or ameliorating the effects of retinitis pigmentosa.

The previous discussion of the background art is intended to facilitate an understanding of the present invention only. The discussion is not an acknowledgement or admission that any of the material referred to is or was part of the common general knowledge as at the priority date of the application.

SUMMARY OF INVENTION

Broadly, according to one aspect of the invention, there is provided an isolated or purified antisense oligomer for modifying pre-mRNA splicing in the CNOT3 gene transcript or part thereof. Preferably, there is provided an isolated or purified antisense oligomer for inducing non-productive splicing in the CNOT3 gene transcript or part thereof.

For example, in one aspect of the invention, there is provided an antisense oligomer of 10 to 50 nucleotides comprising a targeting sequence complementary to a region near or within an intron of the CNOT3 gene transcript or part thereof. In another aspect of the invention, there is provided an antisense oligomer of 10 to 50 nucleotides comprising a targeting sequence complementary to a region near or within an exon of the CNOT3 gene transcript or part thereof.

Preferably, the antisense oligomer is a phosphorodiamidate morpholino oligomer. Preferably the antisense oligomer has a modified backbone.

Preferably, the antisense oligomer is selected from the group comprising the sequences set forth in Table 1.

Preferably, the antisense oligomer is selected from the list comprising: SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64.

The antisense oligomer preferably operates to induce skipping of one or more of the exons of the CNOT3 gene transcript or part thereof. For example, the antisense oligomer may induce skipping of exons 3, 8, 9, 12 and/or 17.

The antisense oligomer of the invention may be selected to be an antisense oligomer capable of binding to a selected CNOT3 target site, wherein the target site is an mRNA splicing site selected from a splice donor site, splice acceptor sites, or exonic splicing elements. The target site may also include some flanking intronic sequences when the donor or acceptor splice sites are targeted.

More specifically, the antisense oligomer may be selected from the group comprising of any one or more of SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64 and/or the sequences set forth in Table 1, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate pre-mRNA processing activity in a CNOT3 gene transcript In certain embodiments, antisense oligomers may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

The invention extends also to a combination of two or more antisense oligomers capable of binding to a selected target to induce exon exclusion in a CNOT3 gene transcript, including a construct comprising two or more such antisense oligomers. The construct may be used for an antisense oligomer-based therapy.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

There is also provided a method for manipulating splicing in a CNOT3 gene transcript, the method including the step of:

a) providing one or more of the antisense oligomers as described herein and allowing the oligomer(s) to bind to a target nucleic acid site.

There is also provided a pharmaceutical, prophylactic, or therapeutic composition to treat, prevent or ameliorate the effects of a disease related to CNOT3 expression in a patient, the composition comprising:

a) one or more antisense oligomers as described herein and b) one or more pharmaceutically acceptable carriers and/or diluents.

The composition may comprise about 1 nM to 1000 nM of each of the desired antisense oligomer(s) of the invention. Preferably, the composition may comprise about 10 nM to 500 nM, most preferably between 1 nM and 10 nM of each of the antisense oligomer(s) of the invention.

There is also provided a method to treat, prevent or ameliorate the effects of a disease associated with CNOT3 expression, comprising the step of:

a) administering to the patient an effective amount of one or more antisense oligomers or pharmaceutical composition comprising one or more antisense oligomers as described herein.

There is also provided the use of purified and isolated antisense oligomers as described herein, for the manufacture of a medicament to treat, prevent or ameliorate the effects of a disease associated with CNOT3 expression.

There is also provided a kit to treat, prevent or ameliorate the effects of a disease associated with CNOT3 expression in a patient, which kit comprises at least an antisense oligomer as described herein and combinations or cocktails thereof, packaged in a suitable container, together with instructions for its use.

Preferably the disease associated with CNOT3 expression in a patient is retinitis pigmentosa. The subject with the disease associated with CNOT3 expression may be a mammal, including a human.

Further aspects of the invention will now be described with reference to the accompanying non-limiting examples and drawings.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 1(a) in-frame exons are depicted by rectangles, whereas exons with junctions that interrupt codons are shown with chevron sides. FIG. 1(b) the CNOT3 protein is represented showing functional domains and amino acid positions corresponding to the exons above. NAR: NOT anchored region. CS: connecting sequence. NOT box: Negative on TATA box. Exclusion of exons 2, 3, 8, 9, 11, 12, 13, 14, 15 and 16 will all disrupt the open reading frame.

FIG. 4A is Pedigree 0255:11 members with PRPF31 mutation (c.267delA). FIG. 4B is Pedigree 0080:13 affected members (c.1205 G>A). Arrow=dermal fibroblasts donated, black=patients currently in the CRE natural history study.

5 are designed to target splice enhancer motifs of CNOT3 exons to mediate the exclusion of target exon(s) during pre-mRNA splicing in order to mediate knockdown of CNOT3 or disrupt protein function. Dermal fibroblasts were transfected for 48 hr with CNOT3 AOs (2'OMe-PS chemistry) targeting exons (as indicated). RT-PCR products were separated on 2% agarose gels.

FIG. 8 shows the negative correlation between CNOT3 and PRPF31 mRNA expression. FIG. 8(*a*) qRT-PCR analysis of PRPF31 and CNOT3 mRNA expression normalised to TATA-binding protein (TBP) expression in iPSCs-derived retinal pigment epithelium from RP11, asymptomatic and healthy (WT) individuals. RP11 and the asymptomatic subject are from the same pedigree, both heterozygous for the PRPF31 c. 1205C>A (Ser402*) mutation. The healthy subject is from an unrelated family. Expression of CNOT3 and PRPF31 mRNA in the healthy control was set to 1. (n≥2). FIG. 8(*b*) Dermal fibroblasts from an RP11 patient were transfected for 48 hr with CNOT3 AOs (2'OMe-PS) targeting exon 4, 6, 7 or 10. PRPF31 transcript level was analysed using qRT-PCR and normalised against TBP expression. PRPF31 expression in cells treated with control AO at 25 nM was set to 1 (n=1). FIG. 8(*c*) Dermal fibroblasts from an RP11 patient were transfected for 48 hr with CNOT3 AOs (2'OMe-PS chemistry) targeting exon 3, 8, 9, 16 or 17. The PRPF31 transcript level was analysed using qRT-PCR and normalised against TBP expression and is shown relative to PRPF31 expression in cells treated with a sham control AO at 25 nM (control PRPF31 expression set to 1 (n=1).

Figure 9A:
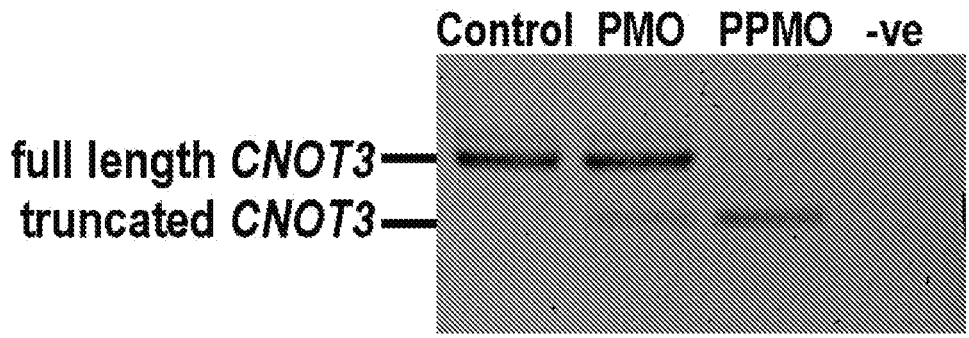
Figure 9B:
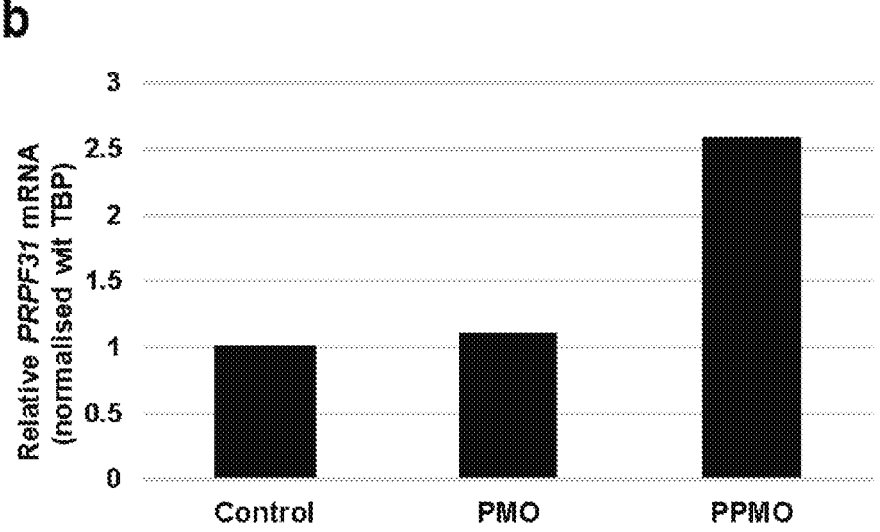

FIG. 9 shows the effect of ASO6 (SEQ ID NO: 64, CNOT3_H17A(+83+107), targeting CNOT3 exon 17) synthesized as phosphorodiamidate morpholino oligomer (PMO) and transfected into RP11 iPSC-derived RPE. (A) CNOT3 exon 17 skipping in cells treated with PMO alone or cell penetrating peptide-tagged PMO (PPMO) at a concentration of 5 µM. (B) PRPF31 upregulation as a consequence of CNOT3 knockdown, determined by qRT-PCR and normalised to TATA-binding protein (TBP) expression. PRPF31 expression in untreated control was set to 1.

Figure 10A:
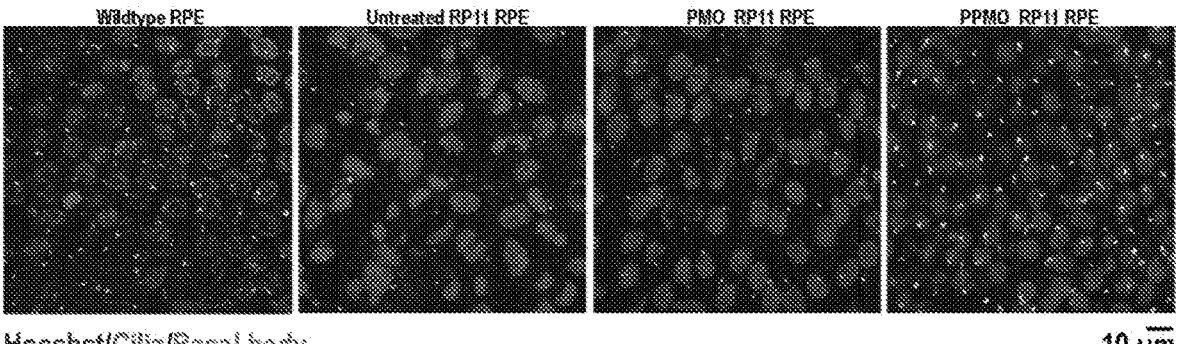
Figure 10B:
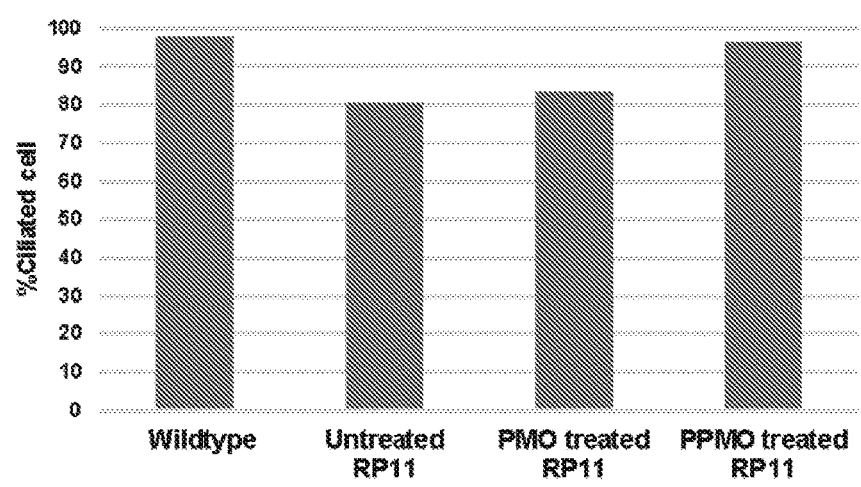
Figure 10C:
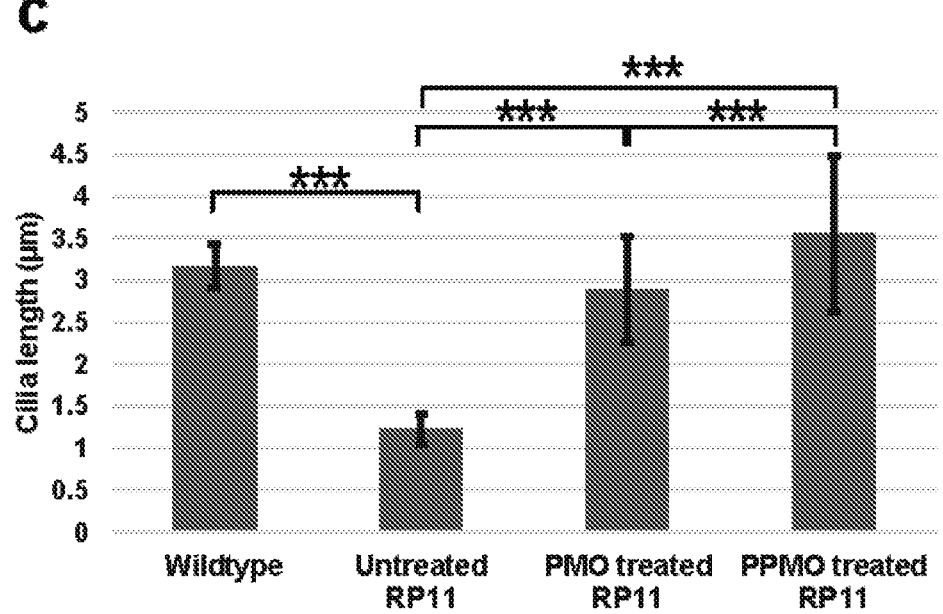

FIG. 10 shows (A) immunostaining of cilia and basal body in wildtype and RP11 RPE with or without antisense oligomer treatment with ASO6 (SEQ ID NO: 64, CNOT3_H17A(+83+107), targeting CNOT3 exon 17). (B) The percentage of RPE cells expressing cilia, counted from >1,000 cells. (C) Cilia length measurement using NIS-Elements Imaging software. Bar chart represents mean±SEM from ~300 ciliated cells. Scale bar=10 µm. Student's t test. ***p<0.001.

DESCRIPTION OF INVENTION

Detailed Description of the Invention

Antisense Oligonucleotides

There is an increased vulnerability of photoreceptors to a generally reduced splicing activity. Whilst mutations in splicing factors may cause splicing deficiency in a variety of tissues, photoreceptor cells would be greatly affected due to their high demand for mRNA production (such as mRNA encoding rhodopsin and other phototransduction proteins). This model presumes that mRNA amounts produced by the retina greatly exceed mRNA levels produced by other tissues.

PRPF31 (also known as hPRP31) encodes an essential pre-mRNA splicing factor required for the assembly and recycling of the U4/U6 RNA complex. Several studies have demonstrated reduced amounts of total PRPF31 mRNA in patients with RP11, as well as delayed rate of spliceosome assembly and pre-mRNA processing. This indicates that the disease occurs via a haplo insufficiency mechanism. In comparison to other tissues, the retina expresses seven times more major spliceosomal small nuclear RNAs (snRNAs).

CCR4-Not transcription complex subunit 3 (CNOT3, one of the five Not proteins of the Ccr4-Not deadenylase complex) has been identified as the main modifier gene determining penetrance of PRPF31 mutations, via a mechanism of transcriptional repression; modulating PRPF31 transcription by directly binding to its promoter. The expression level of the wild-type PRPF31 allele determines whether carriers of the mutated PRPF31 allele are symptomatic. In asymptomatic carriers, CNOT3 is expressed at low levels, allowing higher amounts of wild-type PRPF31 transcripts to be produced and preventing manifestation of retinal degeneration.

Human CNOT3 is an 18-exon gene that codes for a protein with 753 amino acids. Exclusion of exon 2 removes the translation initiation codon from the transcript. Removal of exon 4, 5, 6, 7, 10 or 17 may disrupt functional domains of CNOT3. Exclusion of any of exons 3, 8, 9, and 11-16 disrupts the open reading frame.

Knocking out the CNOT3 gene is embryonically lethal, as it is vital for cell cycle progression through the regulation of mRNA turnover, and the regulation of mRNA decay in various physiological processes. However, if the levels of CNOT3 could be reduced or eliminated locally in the eye of subjects at risk of or suffering from RP, then the progression of the disease would be affected as increased amounts of PRPF31 protein could be produced, mimicking an incomplete penetrance model wherein asymptomatic carriers are protected from the disease by a higher than average expression of PRPF31 from an unmodified gene.

The present invention therefore provides antisense oligonucleotides to induce non-productive splicing or functionally impaired protein of CNOT3 (the negative regulator of PRPF31) to lower (but preferably not ablate) levels of CNOT3 and therefore increase transcription and translation from the normal PRPF31 allele.

In contrast to other antisense oligomer-based therapies, the present invention does not induce increased degradation of RNA via recruitment of RNase H, wherein the RNase H preferentially binds and degraded RNA bound in duplex to DNA of the CNOT3 gene. Nor does it rely on hybridization of the antisense oligomer to the CNOT3 genomic DNA or the binding of antisense oligomers to mRNA to modulate the amount of CNOT3 protein produced by interfering with normal functions such as replication, transcription, translocation and translation.

Rather, the antisense oligomers are used to modify pre-mRNA splicing in a CNOT3 gene transcript or part thereof and induce exon "skipping" and/or terminal intron retention. The strategy preferably reduces total protein expression or generates proteins which lack functional domains, leading to reduced protein function.

According to a first aspect of the invention, there is provided antisense oligomers capable of binding to a selected target on a CNOT3 gene transcript to modify pre-mRNA splicing in a CNOT3 gene transcript or part thereof. Broadly, there is provided an isolated or purified antisense oligomer for inducing targeted exon exclusion and/or terminal intron retention in a CNOT3 gene transcript or part thereof.

In the general population, expression of PRPF31 is highly variable, with levels following a continuous distribution. Expression levels vary from 0.53 to 2.48 arbitrary units, representing a 5-fold variation between lowest and highest expressors. Thirty percent of PRPF31 mutation carriers have no symptoms and these individuals have wild-type alleles that show almost 2-fold higher expression than those with symptomatic PRPF31 mutations. Therefore, preferably the modulation of CNOT3 expression allows at least two-fold higher expression of PRPF31 than those with symptomatic PRPF31 mutations. Preferably the expression of PRPF31 due to the AOs of the invention reducing the expression of CNOT3 is between 1.5- and 5-fold higher than those with symptomatic PRPF31 mutations. For example, the expression of PRPF31 may be between 2- and 4-fold higher.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

An antisense oligomer can be said to be "directed to" or "targeted against" a target sequence with which it hybridizes. In certain embodiments, the target sequence includes a region including a 3' or 5' splice site of a pre-processed mRNA, a branch point, or other sequences involved in the regulation of splicing. The target sequence may be within an exon or within an intron or spanning an intron/exon junction.

In certain embodiments, the antisense oligomer has sufficient sequence complementarity to a target RNA (i.e., the RNA for which splice site selection is modulated) to block a region of a target RNA (e.g., pre-mRNA) in an effective manner. In exemplary embodiments, such blocking of CNOT3 pre-mRNA serves to modulate splicing, either by masking a binding site for a native protein that would otherwise modulate splicing and/or by altering the structure of the targeted RNA. In some embodiments, the target RNA is target pre-mRNA (e.g., CNOT3 gene pre-mRNA).

An antisense oligomer having a sufficient sequence complementarity to a target RNA sequence to modulate splicing of the target RNA means that the antisense oligomer has a sequence sufficient to trigger the masking of a binding site for a native protein that would otherwise modulate splicing and/or alters the three-dimensional structure of the targeted RNA.

Selected antisense oligomers can be made shorter, e.g., about 12 bases, or longer, e.g., about 50 bases, and include a small number of mismatches, as long as the sequence is sufficiently complementary to effect splice modulation upon hybridization to the target sequence, and optionally forms with the RNA a heteroduplex having a Tm of 45° C. or greater.

Preferably, the antisense oligomer is selected from the group comprising the sequences set forth in Table 1. Preferably, the antisense oligomer is selected from the group comprising the sequences in SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64.

In certain embodiments, the degree of complementarity between the target sequence and antisense oligomer is sufficient to form a stable duplex. The region of complementarity of the antisense oligomers with the target RNA sequence may be as short as 8-11 bases, but can be 12-15 bases or more, e.g., 10-50 bases, 10-40 bases, 12-30 bases, 12-25 bases, 15-25 bases, 12-20 bases, or 15-20 bases, including all integers in between these ranges. An antisense oligomer of about 16-17 bases is generally long enough to have a unique complementary sequence. In certain embodiments, a minimum length of complementary bases may be required to achieve the requisite binding Tm, as discussed herein.

In certain embodiments, oligonucleotides as long as 50 bases may be suitable, where at least a minimum number of bases, e.g., 10-12 bases, are complementary to the target sequence. In general, however, facilitated or active uptake in cells is optimized at oligonucleotide lengths of less than about 30 bases. For phosphorodiamidate morpholino oligomer (PMO) antisense oligomers, an optimum balance of binding stability and uptake generally occurs at lengths of 18-25 bases. Included are antisense oligomers (e.g., CPP-MOs, PPMOs, PMOs, PMO-X, PNAs, LNAs, 2'-OMe) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases.

In certain embodiments, antisense oligomers may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that splicing of the target pre-RNA is modulated.

The stability of the duplex formed between an antisense oligomer and a target sequence is a function of the binding Tm and the susceptibility of the duplex to cellular enzymatic cleavage. The Tm of an oligonucleotide with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included.

Additional examples of variants include antisense oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64 or the sequences provided in Table 1.

More specifically, there is provided an antisense oligomer capable of binding to a selected target site to modify pre-mRNA splicing in a CNOT3 gene transcript or part thereof. The antisense oligomer is preferably selected from those provided in Table 1 or SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64.

The modification of pre-mRNA splicing preferably induces "skipping", or the removal of one or more exons or introns of the mRNA and/or terminal intron retention. The resultant protein may be of a shorter length when compared to the parent full-length CNOT3 protein due to either internal truncation or premature termination or may be longer due to terminal intron retention. These CNOT3 proteins may be termed isoforms of the unmodified CNOT3 protein.

The remaining exons of the mRNA generated may be in-frame and produce a shorter protein with a sequence that is similar to that of the parent full length protein, except that it has an internal truncation in a region between the original 3' and 5' ends. In another possibility, the exon skipping may induce a frame shift that results in a protein wherein the first part of the protein is substantially identical to the parent full length protein, but wherein the second part of the protein has a different sequence (eg a nonsense sequence) due to a frame-shift. Alternatively, the exon skipping may induce the production of a prematurely terminated protein due to a disruption of the reading frame and presence of a premature termination of translation. Additionally, the antisense oligomer may produce an artificially lengthened protein, due to in-frame terminal intron retention.

Functional domains of CNOT3 include coiled coil, linker, NAR (Not anchor region), CS (connector sequence) and the NOT box. Exclusion of exon 4 removes part of the coiled coil domain, loss of exon 9 will disrupt the open reading frame, leading to degradation of the mRNA and any encoded protein will be truncated, whereas skipping exon 17 alters the NOT box and is predicted to affect complex formation and therefore CNOT3 function.

The removal of one or more exons may further lead to misfolding of the CNOT3 protein and a reduction in the ability of the protein to be successfully transported through the membrane.

The presence of internally truncated proteins (ie proteins lacking the amino acids encoded by one or more exons) is preferable. If the CNOT3 protein is knocked out, there may be problems with elevation of CNOT3 transcription as the body tries to compensate for the reduction in the total amount of CNOT3 protein. In contrast, the presence of an internally truncated protein (preferably lacking one or more of the features of the complete CNOT3 protein), should be sufficient to prevent elevated transcription, but still provide a therapeutic advantage due to a reduction in the total amount of functional CNOT3 protein.

The antisense oligomer induced exon skipping of the present invention need not completely or even substantially ablate the function of the CNOT3 protein. Preferably, the exon skipping process results in a reduced or compromised functionality of the CNOT3 protein.

The skipping process of the present invention, using antisense oligomers, may skip an individual exon, or may result in skipping two or more exons at once.

The antisense oligomers of the invention may be a combination of two or more antisense oligomers capable of binding to a selected target to induce exon exclusion in a CNOT3 gene transcript. The combination may be a cocktail of two or more antisense oligomers and/or a construct comprising two or more antisense oligomers joined together.

TABLE 1

List of antisense oligonucleotide sequences used in this
study and efficacy score for AO-induced CNOT3 exon skipping.
+1: >50% exon skipping, 0: <50% exon skipping, -1: No exon skipping

| SEQ ID | JSR# | Coordinates | Sequence 5'-3' | 2-OMePS |
|---|---|---|---|---|
| 1 | 4112 | CNOT3_H2A(-6+19) | ACUCUCUUGGAGACGGACGCUGCUA | -1 |
| 2 | 4113 | CNOT3_H2A(+28+52) | AUCUUCCCUGCCCUACAGACGCACU | -1 |
| 3 | 4114 | CNOT3_H2D(+55-4) | GUACCUUGGAGUUUGCGCUUGUCCG | -1 |
| 4 | 3697 | CNOT3_H3A(+9+33) | CGGACACCUUCUUGAGGCAGCGAUC | 1 |
| 5 | 3698 | CNOT3_H3A(+39+63) | GCCAAAUAUCUUCAAACUGCUCCAC | 0 |
| 6 | 4579 | CNOT3_H4A(-8+17) | UUGGCUGCAUUGUGGAGCUGAGGGA | -1 |
| 7 | 4580 | CNOT3_H4A(+12+36) | CUUUUCUUUCUGGUUCGCGUUGGCU | 1 |
| 8 | 4581 | CNOT3_H4A(+38+62) | AUCUCCUUCUUUAGGUCAGCCUCAU | 0 |
| 9 | 4582 | CNOT3_H4D(+13-12) | CAGCCCCCUCACUUGUAGCUUCUUA | 1 |
| 10 | 4583 | CNOT3_H5A(-9+16) | UUUGGUCCCUCAGCCGCUGCAGAUG | -1 |
| 11 | 4584 | CNOT3_H5A(+36+60) | CUGCCUCUUGUCCUUGAUCUCGUUG | 1 |
| 12 | 4585 | CNOT3_H5A(+53+77) | UUGCGGUUGUCUAUAAGCUGCCUCU | -1 |
| 13 | 4586 | CNOT3_H5D(+13-12) | CUGGGCUCCUACCGUCUCAAUGAGC | -1 |
| 14 | 4587 | CNOT3_H6A(-5+20) | ACUUUGAACCGUUCCAUUUGCUGUA | 1 |

TABLE 1-continued

List of antisense oligonucleotide sequences used in this
study and efficacy score for AO-induced CNOT3 exon skipping.
+1: >50% exon skipping, 0: <50% exon skipping, -1: No exon skipping

| SEQ ID | JSR# | Coordinates | Sequence 5'-3' | 2-OMePS |
|---|---|---|---|---|
| 15 | 4588 | CNOT3_H6A(+12+36) | GGUCUCUCGUUCCACAACUUUGAAC | 0 |
| 16 | 4589 | CNOT3_H6A(+37+61) | CCUCUUUGCUGUAAGCUUUGGUUUU | 1 |
| 17 | 4590 | CNOT3_H6A(+89+113) | ACCUCUUCCUUCUCCUUCUGGGCAG | 1 |
| 18 | 4591 | CNOT3_H6D(+15-10) | CCCAACUCACCGUGAGCCACUGGCC | 1 |
| 19 | 4592 | CNOT3_H7A(-6+19) | UGAGCGUGUCGAUGGUAUUCUAGGG | -1 |
| 20 | 4593 | CNOT3_H7A(+16+40) | CAAACUGGUCCACCUGCAUGUUGAG | -1 |
| 21 | 4594 | CNOT3_H7A(+62+86) | CCCUUCUUCUUGCGUGUCUGCACUG | -1 |
| 22 | 4595 | CNOT3_H7D(+15-10) | CCUCACUCACAUCCUUGUCGCCCUU | -1 |
| 23 | 3699 | CNOT3_H8A(-10+15) | CCGCTTCAAGCCCTCGCCCAGGGCC | -1 |
| 24 | 3700 | CNOT3_H8A(+18+41) | GUGGUAGCGGUGCUUCUCGAUGUG | -1 |
| 25 | 3701 | CNOT3_H8A(+34+58) | UGGUCUCUAGCAUGCGCACGUGGUA | -1 |
| 26 | 3702 | CNOT3_H8A(+75+99) | GGCGUCAACGAGGAUGGAGUCAUUG | 0 |
| 27 | 3703 | CNOT3_H8A(+141+165) | CUCCUCGAAGUCGGGGUCCUGGGAU | 1 |
| 28 | 3704 | CNOT3_H9A(-6+19) | GUGGCGACCAGCGCCUGUGCUGUGG | -1 |
| 29 | 3705 | CNOT3_H9A(+29+52) | CUCAUCCUCCAUGUGGCUGUGGCUG | -1 |
| 30 | 3706 | CNOT3_H9A(+56+80) | GGGCGUGCUGCUGGACUGGUUGAAG | 1 |
| 31 | 3707 | CNOT3_H9A(+98+122) | GGCUGGGCUGGGCGGGAUGGGAGAG | 0 |
| 32 | 5485 | CNOT3_H9A(+52+76) | GUGCUGCUGGACUGGUUGAAGAUCU | 0 |
| 33 | 4596 | CNOT3_H10A(-10+15) | AUCUUCAGAGUUUUCCUGAGGUAGG | 1 |
| 34 | 4597 | CNOT3_H10A(+16+40) | CUGUGGAACGUCCCCUCUUCUUAUC | 1 |
| 35 | 4598 | CNOT3_H10D(+12-13) | UCACACCCACCUGGCUGACUUCACU | 1 |
| 36 | 4892 | CNOT3_H11A(+49+73) | AGGUGGGCGGCACAGCUGGGGACUG | -1 |
| 37 | 4893 | CNOT3_H11A(+56+80) | GAGGGGUAGGUGGGCGGCACAGCUG | -1 |
| 38 | 4894 | CNOT3_H11A(+74+98) | GCAGCAGGCGGGGGGCCGGAGGGGU | -1 |
| 39 | 4115 | CNOT3_H11A(-8+17) | CCGUUUUUGGCUGGAGACUGCGGGU | 0 |
| 40 | 4116 | CNOT3_H11A(+171+195) | GUGGCUGGGAGCUGGACUGGCCUUG | 1 |
| 41 | 3708 | CNOT3_H12A(+1+25) | CUGUCUGCCACAACUGAGCUGUAAC | NT |
| 42 | 3709 | CNOT3_H12A(+85+109) | GGGUUGUGGGGGCCGGAAGGGGGGC | NT |
| 43 | 3710 | CNOT3_H12D(+19-6) | ACUCACGAGGUGCUGGGAGGUGGGU | NT |
| 44 | 4117 | CNOT3_H13A(-6+19) | UGCCGCACUGGGUUCCUUCCUGGAG | 1 |
| 45 | 4118 | CNOT3_H13A(+38+62) | UGUUCCCUGAGCCUGGGGCCACGCC | 0 |
| 46 | 4119 | CNOT3_H13A(+83+107) | GAGGAUUCACAGGCAGUGGCACCAG | 1 |
| 47 | 4120 | CNOT3_H14A(-8+17) | CUCAGAGGCUCAGGGGCCUGGGGAG | 0 |
| 48 | 4121 | CNOT3_H14A(+48+72) | AGGGUCCUCAAUGCCAGAGCUGAUG | 0 |
| 49 | 4895 | CNOT3_H15A(+147+171) | GCAUGUGGUGCCAGGCGGCCUCUUC | -1 |
| 50 | 4896 | CNOT3_H15A(+157+181) | GAGGGGUGAGGCAUGUGGUGCCAGG | -1 |
| 51 | 4897 | CNOT3_H15A(+175+199) | CGAAUACGCUCAGAGUCAGAGGGGU | -1 |

TABLE 1-continued

List of antisense oligonucleotide sequences used in this
study and efficacy score for AO-induced CNOT3 exon skipping.
+1: >50% exon skipping, 0: <50% exon skipping, -1: No exon skipping

| SEQ ID | JSR# | Coordinates | Sequence 5'-3' | 2-OMePS |
|--------|------|-------------|----------------|---------|
| 52 | 4122 | CNOT3_H15A(-11+14) | GCUCAGGAUGAUGUCUGUGGGGAGG | -1 |
| 53 | 4123 | CNOT3_H15A(+5+29) | AGGUGCUGAUGUACUGCUCAGGAUG | 1 |
| 54 | 4124 | CNOT3_H15A(+42+66) | CCUCUGACAGCUGCAGGGGCGGCUG | 0 |
| 55 | 4125 | CNOT3_H15A(+78+102) | CCAUGGACAGACACCCAGCGACAGC | 1 |
| 56 | 4126 | CNOT3_H15A(+108+132) | AGAGCUGCUCCUUGGUGAGGGGCAC | 1 |
| 57 | 4127 | CNOT3_H15A(+162+186) | AGUCAGAGGGGUGAGGCAUGUGGUG | 1 |
| 58 | 4128 | CNOT3_H16A(-11+14) | GGGGGAGGUACUGCCUGUGAGAGCA | -1 |
| 59 | 4129 | CNOT3_H16A(+36+58) | GGUGGCAUCUGGUGGUGGUAGG | 1 |
| 60 | 4130 | CNOT3_H16A(+109+133) | CUCCAGAUAGUAGAAGAUGAAGAAG | 0 |
| 61 | 4365 | CNOT3_H17A(+28+52) | GCCAUGACUGCUUCUUUAGGGCCUU | -1 |
| 63 | 4366 | CNOT3_H17A(+57+81) | GAACCACAUCAUGUACUUGGUGUGG | -1 |
| 64 | 4367 | CNOT3_H17A(+83+107) | AUGGUCUUGGGCUCCUCGUGCCUCU | 1 |
| 65 | — | CNOT3_H17A(+78+102) | CUUGGGCUCCUCGUGCCUCUGGAAC | NT |
| 66 | — | CNOT3_H17A(+88+112) | CAGUGAUGGUCUUGGGCUCCUCGUG | NT |
| 67 | 5486 | CNOT3_H17A(+102+126) | CUGCUCAAACUCGUCAGUGAUGGUC | 0 |
| 68 | 3886 | CNOT3_H18A(-10+15) | GUAGAUGUAGGUGCCCUGGCCGGGG | -1 |
| 69 | 3887 | CNOT3_H18A(+16+40) | GCUGGCCCCACUUCUCGUAGUCAAA | 1 |
| 70 | 3888 | CNOT3_H18A(+41+65) | UCAAAGGUGAAGCCUUCCUUCUUCC | 1 |
| 71 | 3889 | CNOT3_H18A(+66+90) | GUCCCGGUCCUCCAGGUAGCGGUAC | -1 |
| 72 | 5551 | CNOT3_H9A(+1+25) | GGGGAGGUGGCGACCAGCGCCUGUG | 0 |
| 73 | 5555 | CNOT3_H17A(+71+95) | UCCUCGUGCCUCUGGAACCACAUCA | 1 |
| 74 | 4368 | CNOT3_H17D(+15-10) | GGGCCCUCACCUGCUCAAACUCGUC | 0 |

There is also provided a method for manipulating splicing in a CNOT3 gene transcript, the method including the step of:

a) providing one or more of the antisense oligomers as described herein and allowing the oligomer(s) to bind to a target nucleic acid site.

According to yet another aspect of the invention, there is provided a splice manipulation target nucleic acid sequence for CNOT3 comprising the DNA equivalents of the nucleic acid sequences selected from Table 1 or the group consisting of SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64, and sequences complementary thereto.

Designing antisense oligomers to completely mask consensus splice sites may not necessarily generate a change in splicing of the targeted exon. Furthermore, the inventors have discovered that size or length of the antisense oligomer itself is not always a primary factor when designing antisense oligomers. With some targets such as IGTA4 exon 3, antisense oligomers as short as 20 bases were able to induce some exon skipping, in certain cases more efficiently than other longer (eg 25 bases) oligomers directed to the same exon.

The inventors have also discovered that there does not appear to be any standard motif that can be blocked or masked by antisense oligomers to redirect splicing. It has been found that antisense oligomers must be designed, and their individual efficacy evaluated empirically.

More specifically, the antisense oligomer may be selected from those set forth in Table 1. The sequences are preferably selected from the group consisting of any one or more of any one or more of SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate pre-mRNA processing activity in a CNOT3 gene transcript.

The oligomer and the DNA, cDNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or pairing such that stable and specific binding occurs between the oligomer and the DNA, cDNA or RNA target. It is understood in the art that the sequence of an antisense oligomer need not be 100% complementary to that of its target sequence to be specifically hybridisable. An antisense oligomer is specifically hybridisable when binding of the compound to the target DNA or RNA molecule interferes with the normal function of the target DNA or RNA product, and there is a sufficient degree of complementarity to avoid non-specific binding of the antisense oligomer to non-target sequences under conditions in which specific binding is desired, i.e., under physiological conditions in the case of in vivo assays or therapeutic treatment, and in the case of in vitro assays, under conditions in which the assays are performed.

Selective hybridisation may be under low, moderate or high stringency conditions, but is preferably under high stringency. Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C., preferably at least 50° C., and typically 60° C.-80° C. or higher. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0). Thus, the antisense oligomers of the present invention may include oligomers that selectively hybridise to the sequences provided in Table 1, or SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64.

It will be appreciated that the codon arrangements at the end of exons in structural proteins may not always break at the end of a codon, consequently there may be a need to delete more than one exon from the pre-mRNA to ensure in-frame reading of the mRNA. In such circumstances, a plurality of antisense oligomers may need to be selected by the method of the invention wherein each is directed to a different region responsible for inducing inclusion of the desired exon and/or intron. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

Typically, selective hybridisation will occur when there is at least about 55% identity over a stretch of at least about 14 nucleotides, preferably at least about 65%, more preferably at least about 75% and most preferably at least about 90%, 95%, 98% or 99% identity with the nucleotides of the antisense oligomer. The length of homology comparison, as described, may be over longer stretches and in certain embodiments will often be over a stretch of at least about nine nucleotides, usually at least about 12 nucleotides, more usually at least about 20, often at least about 21, 22, 23 or 24 nucleotides, at least about 25, 26, 27 or 28 nucleotides, at least about 29, 30, 31 or 32 nucleotides, at least about 36 or more nucleotides.

Thus, the antisense oligomer sequences of the invention preferably have at least 75%, more preferably at least 85%, more preferably at least 86, 87, 88, 89 or 90% homology to the sequences shown in the sequence listings herein. More preferably there is at least 91, 92, 93 94, or 95%, more preferably at least 96, 97, 98% or 99%, homology. Generally, the shorter the length of the antisense oligomer, the greater the homology required to obtain selective hybridisation. Consequently, where an antisense oligomer of the invention consists of less than about 30 nucleotides, it is preferred that the percentage identity is greater than 75%, preferably greater than 85, 86, 87, 88, 89, 90, 91, 92, 93, 94, 95%, 96, 97, 98% or 99% compared with the antisense oligomers set out in the sequence listings herein. Nucleotide homology comparisons may be conducted by sequence comparison programs such as the GCG Wisconsin Bestfit program or GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The antisense oligomer of the present invention may have regions of reduced homology, and regions of exact homology with the target sequence. It is not necessary for an oligomer to have exact homology for its entire length. For example, the oligomer may have continuous stretches of at least 4 or 5 bases that are identical to the target sequence, preferably continuous stretches of at least 6 or 7 bases that are identical to the target sequence, more preferably continuous stretches of at least 8 or 9 bases that are identical to the target sequence. The oligomer may have stretches of at least 10, 11, 12, 13, 14, 15, 16, 17, 18, 19, 20, 21, 22, 23, 24, 25 or 26 bases that are identical to the target sequence. The remaining stretches of oligomer sequence may be intermittently identical with the target sequence; for example, the remaining sequence may have an identical base, followed by a non-identical base, followed by an identical base. Alternatively (or as well) the oligomer sequence may have several stretches of identical sequence (for example 3, 4, 5 or 6 bases) interspersed with stretches of less than perfect homology. Such sequence mismatches will preferably have no or very little loss of splice switching activity.

The term "modulate" or "modulates" includes to "increase" or "decrease" one or more quantifiable parameters, optionally by a defined and/or statistically significant amount. The terms "increase" or "increasing," "enhance" or "enhancing," or "stimulate" or "stimulating" refer generally to the ability of one or antisense oligomers or compositions to produce or cause a greater physiological response (i.e., downstream effects) in a cell or a subject relative to the response caused by either no antisense oligomer or a control compound. The terms "decreasing" or "decrease" refer generally to the ability of one or antisense oligomers or compositions to produce or cause a reduced physiological response (i.e., downstream effects) in a cell or a subject relative to the response caused by either no antisense oligomer or a control compound.

Relevant physiological or cellular responses (in vivo or in vitro) will be apparent to persons skilled in the art, and may include increases in the exclusion of specific exons in a CNOT3-coding pre-mRNA, decreases in the amount of CNOT3-coding pre-mRNA or decreases in the expression of functional CNOT3 protein in a cell, tissue, or subject in need thereof. An "decreased" or "reduced" amount is typically a statistically significant amount, and may include a decrease that is 1.1, 1.2, 2, 3, 4, 5, 6, 7, 8, 9, 10, 15, 20, 30, 40, 50 or more times (e.g., 500, 1000 times) (including all integers and decimal points in between and above 1, e.g., 1.5, 1.6, 1.7. 1.8) less than the amount produced when no antisense oligomer is present (the absence of an agent) or a control compound is used.

The term "reduce" or "inhibit" may relate generally to the ability of one or more antisense oligomers or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a disease such as retinitis pigmentosa.

A "decrease" in a response may be statistically significant as compared to the response produced by no antisense oligomer or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The length of an antisense oligomer may vary, as long as it is capable of binding selectively to the intended location within the pre-mRNA molecule. The length of such sequences can be determined in accordance with selection procedures described herein. Generally, the antisense oligomer will be from about 10 nucleotides in length, up to about 50 nucleotides in length. It will be appreciated, however, that any length of nucleotides within this range may be used in the method. Preferably, the length of the antisense oligomer is between 10 and 40, 10 and 35, 15 to 30 nucleotides in length or 20 to 30 nucleotides in length, most preferably about 25 to 30 nucleotides in length. For example, the oligomer may be 20, 21, 22, 23, 24, 25, 26, 27, 28, 29 or 30 nucleotides in length.

As used herein, an "antisense oligomer" refers to a linear sequence of nucleotides, or nucleotide analogs, that allows the nucleobase to hybridize to a target sequence in an RNA by Watson-Crick base pairing, to form an oligonucleotide: RNA heteroduplex within the target sequence. The terms "antisense oligomer", "antisense oligonucleotide", "oligomer" and "antisense compound" may be used interchangeably to refer to an oligonucleotide. The cyclic subunits may be based on ribose or another pentose sugar or, in certain embodiments, a morpholino group (see description of morpholino oligonucleotides below). Also contemplated are peptide nucleic acids (PNAs), locked nucleic acids (LNAs), and 2'-O-Methyl oligonucleotides, among other antisense agents known in the art.

Included are non-naturally-occurring antisense oligomers, or "oligonucleotide analogs", including antisense oligomers or oligonucleotides having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

One method for producing antisense oligomers is the methylation of the 2' hydroxyribose position and the incorporation of a phosphorothioate backbone produces molecules that superficially resemble RNA but that are much more resistant to nuclease degradation, although persons skilled in the art of the invention will be aware of other forms of suitable backbones that may be useable in the objectives of the invention.

To avoid degradation of pre-mRNA during duplex formation with the antisense oligomers, the antisense oligomers used in the method may be adapted to minimise or prevent cleavage by endogenous RNase H. This property is highly preferred, as the treatment of the RNA with the unmethylated oligomers, either intracellular or in crude extracts that contain RNase H, leads to degradation of the pre-mRNA: antisense oligomer duplexes. Any form of modified antisense oligomers that is capable of by-passing or not inducing such degradation may be used in the present method. The nuclease resistance may be achieved by modifying the antisense oligomers of the invention so that it comprises partially unsaturated aliphatic hydrocarbon chain and one or more polar or charged groups including carboxylic acid groups, ester groups, and alcohol groups.

Antisense oligomers that do not activate RNase H can be made in accordance with known techniques (see, e.g., U.S. Pat. No. 5,149,797). Such antisense oligomers, which may be deoxyribonucleotide or ribonucleotide sequences, simply contain any structural modification which sterically hinders or prevents binding of RNase H to a duplex molecule containing the oligomer as one member thereof, which structural modification does not substantially hinder or disrupt duplex formation. Because the portions of the oligomer involved in duplex formation are substantially different from those portions involved in RNase H binding thereto, numerous antisense oligomers that do not activate RNase H are available. For example, such antisense oligomers may be oligomers wherein at least one, or all, of the inter-nucleotide bridging phosphate residues are modified phosphates, such as methyl phosphonates, methyl phosphorothioates, phosphoromorpholidates, phosphoropiperazidates boranophosphates, amide linkages and phosphoramidates. For example, every other one of the internucleotide bridging phosphate residues may be modified as described. In another non-limiting example, such antisense oligomers are molecules wherein at least one, or all, of the nucleotides contain a 2' lower alkyl moiety (such as, for example, $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

An example of antisense oligomers which when duplexed with RNA are not cleaved by cellular RNase H is 2'-O-methyl derivatives. Such 2'-O-methyl-oligoribonucleotides are stable in a cellular environment and in animal tissues, and their duplexes with RNA have higher Tm values than their ribo- or deoxyribo-counterparts. Alternatively, the nuclease resistant antisense oligomers of the invention may have at least one of the last 3'-terminus nucleotides fluoridated. Still alternatively, the nuclease resistant antisense oligomers of the invention have phosphorothioate bonds linking between at least two of the last 3-terminus nucleotide bases, preferably having phosphorothioate bonds linking between the last four 3'-terminal nucleotide bases.

Increased splice-switching may also be achieved with alternative oligonucleotide chemistry. For example, the antisense oligomer may be chosen from the list comprising: phosphoramidate or phosphorodiamidate morpholino oligomer (PMO); PMO-X; PPMO; peptide nucleic acid (PNA); a locked nucleic acid (LNA) and derivatives including alpha-L-LNA, 2'-amino LNA, 4'-methyl LNA and 4'-O-methyl LNA; ethylene bridged nucleic acids (ENA) and their derivatives; phosphorothioate oligomer; tricyclo-DNA oligomer (tcDNA); tricyclophosphorothioate oligomer; 2'O-Methyl-modified oligomer (2'-OMe); 2'-O-methoxy ethyl (2'-MOE); 2'-fluoro, 2'-fluroarabino (FANA); unlocked nucleic acid (UNA); hexitol nucleic acid (HNA); cyclohexenyl nucleic acid (CeNA); 2'-amino (2'-NH2); 2'-O-ethyl-eneamine or any combination of the foregoing as mixmers or as gapmers. To further improve the delivery efficacy, the above-mentioned modified nucleotides are often conjugated with fatty acids/lipid/cholesterol/amino acids/carbohydrates/polysaccharides/nanoparticles etc. to the sugar or nucleobase moieties. These conjugated nucleotide derivatives can also be used to construct exon skipping antisense oligomers. Antisense oligomer-induced splice modification of the human CNOT3 gene transcripts have generally used either oligoribonucleotides, PNAs, 2OMe or MOE modified bases on a phosphorothioate backbone. Although 2OMeAOs are used for oligo design, due to their efficient uptake in vitro when delivered as cationic lipoplexes, these compounds are susceptible to nuclease degradation and are not considered ideal for in vivo or clinical applications. When alternative chemistries are used to generate the antisense oligomers of the present invention, the uracil (U) of the sequences provided herein may be replaced by a thymine (T).

While the antisense oligomers described above are a preferred form of the antisense oligomers of the present invention, the present invention includes other oligomeric antisense molecules, including but not limited to oligomer mimetics such as are described below.

Specific examples of preferred antisense oligomers useful in this invention include oligomers containing modified backbones or non-natural inter-nucleoside linkages. As defined in this specification, oligomers having modified backbones include those that retain a phosphorus atom in the backbone and those that do not have a phosphorus atom in the backbone. For the purposes of this specification, and as sometimes referenced in the art, modified oligomers that do not have a phosphorus atom in their inter-nucleoside backbone can also be considered to be antisense oligomers.

In other preferred oligomer mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligomer mimetic that has been shown to have excellent hybridization properties, is referred to as a peptide nucleic acid (PNA). In PNA compounds, the sugar-backbone of an oligomer is replaced with an amide containing backbone, in particular an aminoethylglycine backbone. The nucleo-bases are retained and are bound directly or indirectly to aza nitrogen atoms of the amide portion of the backbone.

Another preferred chemistry is the phosphorodiamidate morpholino oligomer (PMO) oligomeric compounds, which are not degraded by any known nuclease or protease. These compounds are uncharged, do not activate RNase H activity when bound to a RNA strand and have been shown to exert sustained splice modulation after in vivo administration (Summerton and Weller, Antisense Nucleic Acid Drug Development, 7, 187-197).

Modified oligomers may also contain one or more substituted sugar moieties. Oligomers may also include nucleobase (often referred to in the art simply as "base") modifications or substitutions. Certain nucleobases are particularly useful for increasing the binding affinity of the oligomeric compounds of the invention. These include 5-substituted pyrimidines, 6-azapyrimidines, and N-2, N-6 and O-6 substituted purines, including 2-aminopropyladenine, 5-propynyluracil and 5-propynylcytosine. 5-methylcytosine substitutions have been shown to increase nucleic acid duplex stability by $0.6\text{-}1.2°$ C., even more particularly when combined with 2'-O-methoxyethyl sugar modifications.

Another modification of the oligomers of the invention involves chemically linking to the oligomer one or more moieties or conjugates that enhance the activity, cellular distribution or cellular uptake of the oligomer. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, myristyl, or an octadecylamine or hexylamino-carbonyl-oxycholesterol moiety.

Cell penetrating peptides have been added to phosphorodiamidate morpholino oligomers to enhance cellular uptake and nuclear localization. Different peptide tags have been shown to influence efficiency of uptake and target tissue specificity, as shown in Jearawiriyapaisarn et al. (2008), Mol. Ther. 16 9, 1624-1629.

It is not necessary for all positions in a given compound to be uniformly modified, and in fact more than one of the aforementioned modifications may be incorporated in a single compound or even at a single nucleoside within an oligomer. The present invention also includes antisense oligomers that are chimeric compounds. "Chimeric" antisense oligomers or "chimeras," in the context of this invention, are antisense oligomers, particularly oligomers, which contain two or more chemically distinct regions, each made up of at least one monomer unit, i.e., a nucleotide in the case of an oligomer compound. These oligomers typically contain at least one region wherein the oligomer is modified so as to confer upon the oligomer or antisense oligomer increased resistance to nuclease degradation, increased cellular uptake, and an additional region for increased binding affinity for the target nucleic acid.

The activity of antisense oligomers and variants thereof can be assayed according to routine techniques in the art. For example, splice forms and expression levels of surveyed RNAs and proteins may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed polynucleotide) from a cell, tissue or organism, and by hybridizing the mRNA/ cDNA with a reference polynucleotide, which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

The present invention provides antisense oligomer induced splice-switching of the CNOT3 gene transcript, clinically relevant oligomer chemistries and delivery systems to direct CNOT3 splice manipulation to therapeutic levels. Substantial decreases in the amount of full length CNOT3 mRNA, and hence CNOT3 protein from CNOT3 gene transcription, are achieved by:

1) oligomer refinement in vitro using fibroblast cell lines, through experimental assessment of (i) intronic-enhancer target motifs, (ii) antisense oligomer length and development of oligomer cocktails, (iii) choice of chemistry, and (iv) the addition of cell-penetrating peptides (CPP) to enhance oligomer delivery; and 2) detailed evaluation of a novel approach to generate CNOT3 transcripts with one or more missing exons.

As such, it is demonstrated herein that processing of CNOT3 pre-mRNA can be manipulated with specific antisense oligomers. In this way functionally significant decreases in the amount of CNOT3 protein can be obtained, thereby reducing the severe pathology associated with retinitis pigmentosa.

The antisense oligomers used in accordance with this invention may be conveniently made through the well-known technique of solid phase synthesis. Equipment for such synthesis is sold by several vendors including, for example, Applied Biosystems (Foster City, Calif.). One method for synthesising oligomers on a modified solid support is described in U.S. Pat. No. 4,458,066.

Any other means for such synthesis known in the art may additionally or alternatively be employed. It is well known to use similar techniques to prepare oligomers such as the phosphorothioates and alkylated derivatives. In one such automated embodiment, diethyl-phosphoramidites are used as starting materials and may be synthesized as described by Beaucage, et al., (1981) Tetrahedron Letters, 22:1859-1862.

The antisense oligomers of the invention are synthesised in vitro and do not include antisense compositions of biological origin, or genetic vector constructs designed to direct the in vivo synthesis of antisense oligomers. The molecules of the invention may also be mixed, encapsulated, conjugated or otherwise associated with other molecules, molecule structures or mixtures of compounds, as for example, liposomes, receptor targeted molecules etc.

The antisense oligomers may be formulated for oral, topical, parenteral or other delivery, particularly formulations for topical ocular and injectable ocular delivery. The formulations may be formulated for assisting in uptake, distribution and/or absorption at the site of delivery or activity. Preferably the antisense oligomers of the present invention are formulated for delivered topically to the eye or by intraocular injection or intraocular implant, so that the effects on CNOT3 production are spatially limited and are not systemic.

Method of Treatment

According to a still further aspect of the invention, there is provided one or more antisense oligomers as described herein for use in an antisense oligomer-based therapy. Preferably, the therapy is for a condition related to CNOT3 expression. More preferably, the therapy for a condition related to CNOT3 expression is therapy for retinitis pigmentosa.

More specifically, the antisense oligomer may be selected from Table 1, or the group consisting of any one or more of SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate pre-mRNA processing activity in a CNOT3 gene transcript.

The invention extends also to a combination of two or more antisense oligomers capable of binding to a selected target to induce exon exclusion in a CNOT3 gene transcript. The combination may be a cocktail of two or more antisense oligomers, a construct comprising two or more or two or more antisense oligomers joined together for use in an antisense oligomer-based therapy.

There is therefore provided a method to treat, prevent or ameliorate the effects of a disease associated with CNOT3 expression, comprising the step of:

a) administering to the patient an effective amount of one or more antisense oligomers or pharmaceutical composition comprising one or more antisense oligomers as described herein.

Preferably the disease associated with CNOT3 expression in a patient is retinitis pigmentosa.

Therefore, the invention provides a method to treat, prevent or ameliorate the effects of retinitis pigmentosa, comprising the step of:

a) administering to the patient an effective amount of one or more antisense oligomers or pharmaceutical composition comprising one or more antisense oligomers as described herein.

Preferably, the therapy is used to reduce the levels of functional CNOT4 protein via an exon skipping strategy. The reduction in levels of CNOT3 is preferably achieved by reducing the transcripts level through modifying pre-mRNA splicing in the CNOT3 gene transcript or part thereof.

The reduction in CNOT3 will preferably lead to a reduction in the quantity, duration or severity of the symptoms of a CNOT3-related condition or pathology, such as retinitis pigmentosa.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The subject with the disease associated with CNOT3 expression may be a mammal, including a human.

The antisense oligomers of the present invention may also be used in conjunction with alternative therapies, such as drug therapies.

The present invention therefore provides a method of treating, preventing or ameliorating the effects of a disease or condition associated with CNOT3 expression, wherein the antisense oligomers of the present invention and administered sequentially or concurrently with another alternative therapy associated with treating, preventing or ameliorating the effects of a disease or condition associated with CNOT3 expression. Preferably, the disease or condition is retinitis pigmentosa.

Delivery

The antisense oligomers of the present invention also can be used as a prophylactic or therapeutic, which may be utilised for the purpose of treatment of a disease. Accordingly, in one embodiment the present invention provides antisense oligomers that bind to a selected target in the CNOT3 pre-mRNA to induce efficient and consistent exon skipping as described herein, in a therapeutically effective amount, admixed with a pharmaceutically acceptable carrier, diluent, or excipient.

There is also provided a pharmaceutical, prophylactic, or therapeutic composition to treat, prevent or ameliorate the effects of a disease related to CNOT3 expression in a patient, the composition comprising:

a) one or more antisense oligomers as described herein; and b) one or more pharmaceutically acceptable carriers and/or diluents.

Preferably, the antisense oligomer of the present invention is delivered via a localised ocular route to avoid a systemic effect. Routes of administration include, but are not limited to, intravitreal, intracameral, subconjunctival, subtenon, retrobulbar, posterior juxtascleral, or topical (drops, eye washes, creams etc). Delivery methods include, for example, injection by a syringe and a drug delivery device, such as an implanted vitreal delivery device (i.e., VITRASERT®).

In one embodiment, the antisense oligomer is administered intravenously at a dose of 20 mg/kg. For example, the antisense oligomer may be administered intravenously at a dose of 20 mg/kg in a mouse.

Preferably, the antisense oligomer is administered via intravitreal injection at between 0.01-1.5 mg/kg body weight, between 0.1-0.1 mg/kg body weight, between 0.2-0.8 mg/kg body weight, between 0.4-0.7 mg/kg body weight, or more preferably between 0.4-0.6 mg/kg body weight. The antisense oligomer may be administered via intravitreal injection at, for example, about 0.05 mg/kg body weight, 0.1 mg/kg body weight, 0.2 mg/kg body weight, 0.3 mg/kg body weight, 0.4 mg/kg body weight, 0.5 mg/kg body weight, 0.6 mg/kg body weight, 0.7 mg/kg body weight, 0.8 mg/kg body weight, 0.9 mg/kg body weight, 1.0 mg/kg body weight, 1.1 mg/kg body weight, 1.2 mg/kg body weight, 1.3 mg/kg body weight, 1.4 mg/kg body weight, 1.5 mg/kg body weight. Preferably, the antisense oligomer is administered via intravitreal injection at about 0.5 mg/kg body weight. For example, the antisense oligomer may be administered via intravitreal injection at about 0.5 mg/kg body weight to a mouse.

More preferably, the antisense oligomer is administered via intravitreal injection at between 0.5-50 mg per eye, 0.5-40 mg per eye, 0.5-30 mg per eye, 2-30 mg per eye, 2-20 mg per eye, 0.5-20 mg per eye, or more preferably between 5-20 mg per eye. The antisense oligomer may be administered via intravitreal injection at, for example, about 0.5 mg per eye, 1.0 mg per eye, 2.0 mg per eye, 3.0 mg per eye, 4.0 mg per eye, 5.0 mg per eye, 6.0 mg per eye, 7.0 mg per eye, 8.0 mg per eye, 9.0 mg per eye, 10.0 mg per eye, 11.0 mg per eye, 12.0 mg per eye, 13.0 mg per eye, 14.0 mg per eye, 15.0 mg per eye, 16.0 mg per eye, 17.0 mg per eye, 18.0 mg per eye, 19.0 mg per eye, 20.0 mg per eye, 21 mg per eye, 22 mg per eye, 23 mg per eye, 24 mg per eye, 25 mg per eye, 30 mg per eye, 35 mg per eye, 40 mg per eye, 45 mg per eye, or 50 mg per eye. Preferably, the antisense oligomer is administered via intravitreal injection at about 5-20 mg per eye.

The antisense oligomer may be administered at regular intervals for a short time period, e.g., daily for two weeks or less. However, in many cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

Dosing may be dependent on severity and responsiveness of the disease state to be treated, with the course of treatment lasting from several days to several months, or until a cure is effected or a diminution of the disease state is achieved. Alternatively, dosing may be titrated against disease progression rate. A baseline progression is established. Then the progression rate after an initial once off dose is monitored to check that there is a reduction in the rate. Preferably, there is no progression after dosing. Preferably, re-dosing is only necessary if progression rate is unchanged. Successful treatment preferably results in no further progression of the disease or even some recovery of vision. Optimal dosing schedules can be calculated from measurements of drug accumulation in the body of the patient. Persons of ordinary skill can easily determine optimum dosages, dosing methodologies and repetition rates.

Optimum dosages may vary depending on the relative potency of individual oligomers, and can generally be estimated based on EC50s found to be effective in in vitro and in vivo animal models.

In general, dosage is from 0.01-1.5 mg/kg body weight or administration via intravitreal injection at between 0.5-50 mg per eye and may be given once or more daily, weekly, monthly or yearly, or even once every 2 to 20 years. Repetition rates for dosing depend on progression rate of the disease. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, the dose may be 0.01-1.5 mg/kg body weight or administration via intravitreal injection at between 0.5-50 mg per eye, once or more daily, weekly, monthly or yearly, or even once every 2 to 20 years.

An effective in vivo treatment regimen using the antisense oligomers of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomers of the invention may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

Intranuclear oligomer delivery is a major challenge for antisense oligomers. Different cell-penetrating peptides (CPP) localize PMOs to varying degrees in different conditions and cell lines, and novel CPPs have been evaluated by the inventors for their ability to deliver PMOs to the target cells. The terms CPP or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. CPPs are well-known in the art and are disclosed, for example in U.S. Application No. 2010/0016215, which is incorporated by reference in its entirety.

The present invention therefore provides antisense oligomers of the present invention win combination with cell-penetrating peptides for manufacturing therapeutic pharmaceutical compositions.

Excipients

The antisense oligomers of the present invention are preferably delivered in a pharmaceutically acceptable composition. The composition may comprise about 1 nM to 1000 nM of each of the desired antisense oligomer(s) of the invention. Preferably, the composition may comprise about 1 nM to 500 nM, 10 nM to 500 nM, 50 nM to 750 nM, 10 nM to 500 nM, 1 nM to 100 nM, 1 nM to 50 nM, 1 nM to 40 nM, 1 nM to 30 nM, 1 nM to 20 nM, most preferably between 1 nM and 10 nM of each of the antisense oligomer(s) of the invention.

The composition may comprise about 1 nm, 2 nm, 3 nm, 4 nm, 5 nm, 6 nm, 7 nm, 8 nm, 9 nm, 10 nm, 20 nm, 50 nm, 75 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm of each of the desired antisense oligomer(s) of the invention.

The present invention further provides one or more antisense oligomers adapted to aid in the prophylactic or therapeutic treatment, prevention or amelioration of symptoms of a disease such as an CNOT3 expression related disease or pathology in a form suitable for delivery to a patient.

The phrase "pharmaceutically acceptable" refers to molecular entities and compositions that are physiologically tolerable and do not typically produce an allergic or similarly untoward reaction, such as gastric upset and the like, when administered to a patient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in *Remington: The Science and Practice of Pharmacy,* 22nd Ed., Pharmaceutical Press, PA (2013).

In a more specific form of the invention there are provided pharmaceutical compositions comprising therapeutically effective amounts of one or more antisense oligomers of the invention together with pharmaceutically acceptable diluents, preservatives, solubilizers, emulsifiers, adjuvants, and/or carriers. Such compositions include diluents of various buffer content (e.g. Tris-HCl, acetate, phosphate), pH and ionic strength and additives such as detergents and solubilizing agents (e.g. Tween 80, Polysorbate 80), antioxidants (e.g., ascorbic acid, sodium metabisulfite), preservatives (e.g. Thimersol, benzyl alcohol) and bulking substances (e.g., lactose, mannitol). The material may be incorporated into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present proteins and derivatives. See, for example, *Remington: The Science and Practice of Pharmacy,* 22nd Ed., Pharmaceutical Press, PA (2013). The compositions may be prepared in liquid form, or may be in dried powder, such as a lyophilised form.

It will be appreciated that pharmaceutical compositions provided according to the present invention may be administered by any means known in the art. The pharmaceutical compositions for administration are administered by injection, orally, topically or by the pulmonary or nasal route. For example, the antisense oligomers may be delivered by intravenous, intra-arterial, intraperitoneal, intramuscular or subcutaneous routes of administration. The appropriate route may be determined by one of skill in the art, as appropriate to the condition of the subject under treatment. Preferably, the antisense oligomers are delivered topically to the eye or by intraocular injection or intraocular implant, so that the effects on CNOT3 production are spatially limited and are not systemic.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860 and/or U.S. patent application Ser. No. 09/315, 298 filed on May 20, 1999.

In certain embodiments, the antisense oligomers of the disclosure can be delivered by topical or transdermal methods (e.g., via incorporation of the antisense oligomers into, e.g., emulsions, with such antisense oligomers optionally packaged into liposomes) including delivery to ocular surfaces. Such topical or transdermal and emulsion/liposome-mediated methods of delivery are described for delivery of antisense oligomers in the art, e.g., in U.S. Pat. No. 6,965, 025. Preferably the topical delivery is delivery to the eye.

The antisense oligomers described herein may also be delivered via an implantable device. Design of such a device is an art-recognized process, with, e.g., synthetic implant design described in, e.g., U.S. Pat. No. 6,969,400. Preferably the implant is able to be implanted into the eye for sustained delivery of the antisense oligomers.

Compositions and formulations for ocular administration, including ocular injection, topical ocular delivery and ocular implant may include sterile aqueous solutions which may also contain buffers, diluents and other suitable additives such as, but not limited to, penetration enhancers, carrier compounds and other pharmaceutically acceptable carriers or excipients.

The delivery of a therapeutically useful amount of anti- sense oligomers may be achieved by methods previously published. For example, delivery of the antisense oligomer may be via a composition comprising an admixture of the antisense oligomer and an effective amount of a block copolymer. An example of this method is described in US patent application US20040248833. Other methods of deliv- ery of antisense oligomers to the nucleus are described in Mann C J et al. (2001) Proc, Natl. Acad. Science, 98 (1) 42-47, and in Gebski et al. (2003) Human Molecular Genet- ics, 12 (15): 1801-1811. A method for introducing a nucleic acid molecule into a cell by way of an expression vector either as naked DNA or complexed to lipid carriers, is described in U.S. Pat. No. 6,806,084.

Antisense oligomers can be introduced into cells using art-recognized techniques (e.g., transfection, electropora- tion, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

It may be desirable to deliver the antisense oligomer in a colloidal dispersion system. Colloidal dispersion systems include macromolecule complexes, nanocapsules, micro- spheres, beads, and lipid-based systems including oil-in- water emulsions, micelles, mixed micelles, and liposomes or liposome formulations. These colloidal dispersion systems can be used in the manufacture of therapeutic pharmaceu- tical compositions.

Liposomes are artificial membrane vesicles, which are useful as delivery vehicles in vitro and in vivo. These formulations may have net cationic, anionic, or neutral charge characteristics and have useful characteristics for in vitro, in vivo and ex vivo delivery methods. It has been shown that large unilamellar vesicles can encapsulate a substantial percentage of an aqueous buffer containing large macromolecules. RNA and DNA can be encapsulated within the aqueous interior and be delivered to cells in a biologi- cally active form (Fraley, et al., Trends Biochem. Sci. 6:77, 1981).

In order for a liposome to be an efficient gene transfer vehicle, the following characteristics should be present: (1) encapsulation of the antisense oligomer of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a com- bination of phospholipids, particularly high phase-transi- tion-temperature phospholipids, usually in combination with steroids, especially cholesterol. Other phospholipids or other lipids may also be used. The physical characteristics of liposomes depend on pH, ionic strength, and the presence of divalent cations. Cationic liposomes are positively charged liposomes which are believed to interact with negatively charged DNA molecules to form a stable complex. Lipo- somes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

As known in the art, antisense oligomers may be delivered using, for example, methods involving liposome-mediated uptake, lipid conjugates, polylysine-mediated uptake, nan- oparticle-mediated uptake, and receptor-mediated endocy- tosis, as well as additional non-endocytic modes of delivery, such as microinjection, permeabilization (e.g., streptoly- sin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The antisense oligomer may also be combined with other pharmaceutically acceptable carriers or diluents to produce a pharmaceutical composition. Suitable carriers and diluents include isotonic saline solutions, for example phosphate- buffered saline. The composition may be formulated for parenteral, intramuscular, intravenous, subcutaneous, intraocular, oral, or transdermal administration.

The routes of administration described are intended only as a guide since a skilled practitioner will be able to readily determine the optimum route of administration and any dosage for any particular animal and condition.

Multiple approaches for introducing functional new genetic material into cells, both in vitro and in vivo have been attempted (Friedmann (1989) Science, 244:1275- 1280). These approaches include integration of the gene to be expressed into modified retroviruses (Friedmann (1989) supra; Rosenberg (1991) Cancer Research 51 (18), suppl.: 5074S-5079S); integration into non-retrovirus vectors (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand- specific, cation-based transport systems (Wu and Wu (1988) J. Biol. Chem., 263:14621-14624) or the use of naked DNA, expression vectors (Nabel et al. (1990), supra); Wolff et al. (1990) Science, 247:1465-1468). Direct injection of trans- genes into tissue produces only localized expression (Rosen- feld (1992) supra); Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (ab- stract)) have reported in vivo transfection only of lungs of mice following either intravenous or intratracheal administration of a DNA liposome complex. An example of a review article of human gene therapy procedures is: Anderson, Science (1992) 256:808-813; Barteau et al. (2008), Curr Gene Ther; 8 (5): 313-23; Mueller et al. (2008). Clin Rev Allergy Immunol; 35 (3): 164-78; Li et al. (2006) Gene Ther., 13 (18): 1313-9; Simoes et al. (2005) Expert Opin Drug Deliv; 2 (2): 237-54.

The antisense oligomers of the invention encompass any pharmaceutically acceptable salts, esters, or salts of such esters, or any other compound which, upon administration to an animal including a human, is capable of providing (directly or indirectly) the biologically active metabolite or residue thereof. Accordingly, as an example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e. salts that retain the desired biological activity of the parent compound and do not impart undesired toxicological effects thereto. For oligomers, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be via topical (including ophthalmic and mucous membranes, as well as rectal delivery), pulmonary (e.g., by inhalation or insufflation of powders or aerosols, including by nebulizer, intratracheal, intranasal, epidermal and transdermal), oral or parenteral routes. Parenteral administration includes intravenous, intra-arterial, subcutaneous, intraperitoneal, intraocular or intramuscular injection or infusion; or intracranial, e.g., intrathecal or intraventricular, administration. Oligomers with at least one 2'-O-methoxyethyl modification are believed to be particularly useful for intraocular administration. Preferably, the antisense oligomer is delivered via the intraocular route.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

Swiss-Style

According to another aspect of the invention there is provided the use of one or more antisense oligomers as described herein in the manufacture of a medicament for the modulation or control of a disease associated with CNOT3 expression.

The invention also provides for the use of purified and isolated antisense oligomers as described herein, for the manufacture of a medicament for treatment of a disease associated with CNOT3 expression.

There is also provided the use of purified and isolated antisense oligomers as described herein, for the manufacture of a medicament to treat, prevent or ameliorate the effects of a disease associated with CNOT3 expression.

Preferably, the CNOT3-related pathology or disease is retinitis pigmentosa.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

Kits

There is also provided a kit to treat, prevent or ameliorate the effects of a disease associated with CNOT3 expression in a patient, which kit comprises at least an antisense oligomer as described herein and combinations or cocktails thereof, packaged in a suitable container, together with instructions for its use.

In a preferred embodiment, the kits will contain at least one antisense oligomer as described herein or as shown in Table 1, or SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64 or a cocktail of antisense oligomers, as described herein. The kits may also contain peripheral reagents such as buffers, stabilizers, etc.

There is therefore provided a kit to treat, prevent or ameliorate a disease or condition associated with CNOT3 expression in a patient, which kit comprises at least an antisense oligomer described herein or as shown in Table 1 and combinations or cocktails thereof, packaged in a suitable container, together with instructions for its use.

There is also provided a kit to treat, prevent or ameliorate a disease or condition associated with CNOT3 expression in a patient, which kit comprises at least an antisense oligomer selected from the group consisting of any one or more of SEQ ID NOs: 1-74, more preferably SEQ ID NOs: 4, 7, 9, 11, 14, 16-18, 27, 30, 34, 35, 64 and 67 even more preferably SEQ ID NOs: 4, 7, 27, 30, 34 and 64, and combinations or cocktails thereof, packaged in a suitable container, together with instructions for its use.

Preferably, the disease or condition is retinitis pigmentosa.

The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. For in vivo use, the expression construct may be formulated into a pharmaceutically acceptable syringeable composition. In this case the container means may itself be an inhalant, syringe, pipette, eye dropper, or other such like apparatus, from which the formulation may be applied to an affected area of the animal, such as the lungs, injected into an animal, or even applied to and mixed with the other components of the kit.

In an embodiment, the kit of the present invention comprises a composition comprising a therapeutically effective amount of an antisense oligomer capable of binding to a selected target on a CNOT3 gene transcript to modify pre-mRNA splicing in a CNOT3 gene transcript or part thereof. In an alternative embodiment, the formulation is in pre-measured, pre-mixed and/or pre-packaged. Preferably, the intraocular solution is sterile.

The kit of the present invention may also include instructions designed to facilitate user compliance. Instructions, as used herein, refers to any label, insert, etc., and may be positioned on one or more surfaces of the packaging material, or the instructions may be provided on a separate sheet, or any combination thereof. For example, in an embodiment, the kit of the present invention comprises instructions for administering the formulations of the present invention. In one embodiment, the instructions indicate that the formulation of the present invention is suitable for the treatment of retinitis pigmentosa. Such instructions may also include instructions on dosage, as well as instructions for administration via topical delivery to the eye or via intraocular injection.

The antisense oligomers and suitable excipients can be packaged individually so to allow a practitioner or user to formulate the components into a pharmaceutically acceptable composition as needed. Alternatively, the antisense oligomers and suitable excipients can be packaged together, thereby requiring de minimus formulation by the practitioner or user. In any event, the packaging should maintain chemical, physical, and aesthetic integrity of the active ingredients.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. Size, displacement and field strength etc). A range of values will be understood to include all values within the range, including the values defining the range, and values adjacent to the range which lead to the same or substantially the same outcome as the values immediately adjacent to that value which defines the boundary to the range. Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

Sequence identity numbers ("SEQ ID NO:") containing nucleotide and amino acid sequence information included in this specification are collected at the end of the description and have been prepared using the program Patent In Version 3.0. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

An antisense oligomer nomenclature system was proposed and published to distinguish between the different antisense oligomers (see Mann et al., (2002) J Gen Med 4, 644-654). This nomenclature became especially relevant when testing several slightly different antisense oligomers, all directed at the same target region, as shown below:

H #A/D (x:y)

the first letter designates the species (e.g. H: human, M: murine)

"#" designates target exon number

"A/D" indicates acceptor or donor splice site at the beginning and end of the exon, respectively (x y) represents the annealing coordinates where "−" or "+" indicate intronic or exonic sequences respectively. As an example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2−18) where the last 2 exonic bases and the first 18 intronic bases correspond to the annealing site of the antisense oligomer. Entirely exonic annealing coordinates that would be represented by A(+65+85), that is the site between the 65th and 85th nucleotide, inclusive, from the start of that exon.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Example 1

AO Mediated Exon Skipping to Induce a Frame-Shift in CNOT3

Figure 1:
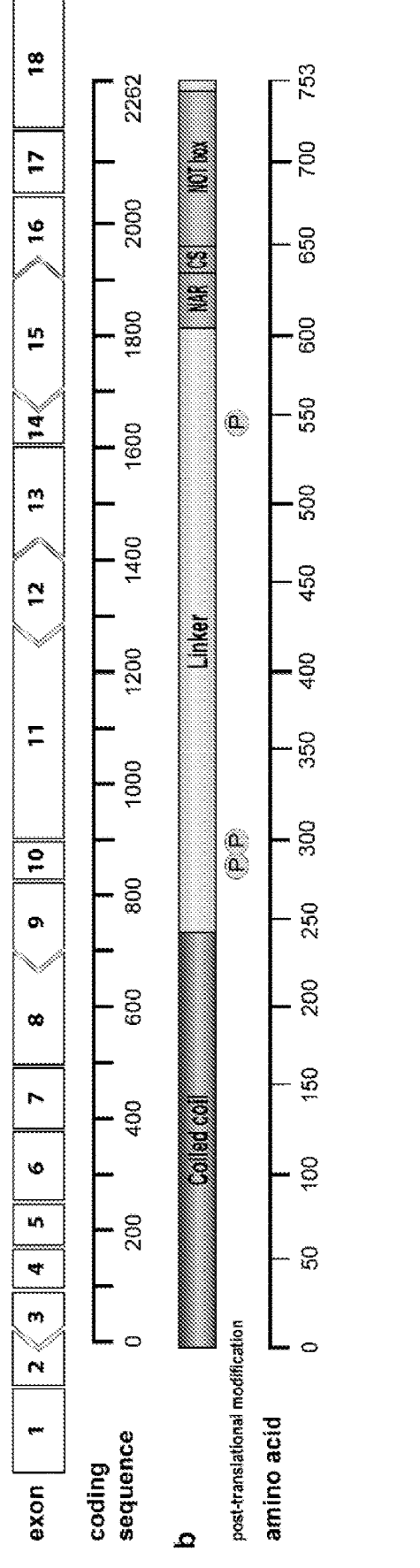
FIG. 1 is a schematic of the CNOT3 reading frame. CNOT3 consists of 18 exons and encodes a protein with 753 amino acids.

The exon structure of CNOT3 is shown in FIG. 1. Splice switching AOs were designed to target enhancer sites within frame-shifting exons in CNOT3 pre-mRNA (FIG. 1), to induce exon skipping and consequently, loss of the open reading frame and knockdown of CNOT3.

Normal human fibroblasts and fibroblasts from an RP11 patient (PRPF31 c.1205 C>A Ser402*) were obtained from skin biopsies and cultured in DMEM supplemented with 10% FBS. Antisense sequences (Table 1), synthesised in-house as 2'O-Methyl phosphorothioate oligomers were transfected into fibroblasts in 24 well plates as lipoplexes using Lipofectamine 3000 (Life Technologies), as per the manufacturer's instructions. Sequences that were effective in altering target exon selection were then synthesized as phosphorodiamidate morpholino oligomers (PMO) and transfected into fibroblasts as i) uncomplexed ii) annealed to a sense ODN leash and delivered with Lipofectamine 3000 (as above), or iii) nucleofection using the P2 Primary cell 4-D Nucleofector X kit S (Lonza), as per manufacturer's instructions.

Total RNA was extracted from the transfected and control cells using the MagMax RNA extraction system (Life Technologies). Transcripts of interest are assessed by semiquantitative RT-PCR in the first instance, and then by qRT-PCR. cDNA (RNA 300 ng) was synthesised, as per manufacturer's instructions, using SuperScript IV reverse transcriptase kit (Life Technologies). RT-PCRs were done using LA Taq DNA polymerase with GC buffer I (TAKARA), as per the manufacturer's instructions.

Three different primer sets were used to assess CNOT3 transcripts after cells were transfected with the CNOT3 exon skipping AOs:

1. For AOs targeting exon 3, a forward primer annealing to exon 2 was paired with a reverse primer in exon 6.
2. For AOs targeting exons 8 and 9, a forward primer in exon 7 was paired with an exon 11 reverse primer.
3. For AOs targeting exons 16 and 17, a forward primer in exon 15 was paired with a reverse primer in exon 18.

qRT-PCR was used to quantitate PRPF31 transcript levels after transfection with the CNOT3 exon skipping AOs. A forward primer across the PRPF31 exon 2 and 3 junction was paired with a reverse primer across the exon 3 and 4 junction (Table 2). Results for all CNOT3 AO treated cells were normalised to the expression of two housekeeping genes, TBP and GAPDH, and compared to Anti ISS-N1 and sham AO treated cells in order to calculate fold-changes in PRPF31 transcripts.

TABLE 2

Primers for RT-PCR and qRT-PCR of CNOT3, PRPF31 and housekeeping genes, TBP and GAPDH.

| SEQ ID NO | Gene | Primer name | Primer sequence 5'-3' | Conc. | Analysis |
|---|---|---|---|---|---|
| 75 | CNOT3 | Exon 2 Forward | GAAGATGGCGGACAAGCGCAA | 50 nM | RT-PCR |
| 76 | CNOT3 | Exon 6 Reverse | CTGGCCAACCTCTTCCTTCTC | 50 nM | RT-PCR |
| 77 | CNOT3 | Exon 7 Forward | CTGTCAGTGCAGACACGCAA | 50 nM | RT-PCR |
| 78 | CNOT3 | Exon 11 Reverse | GGACAGGCTGGAGCCGTTT | 50 nM | RT-PCR |
| 79 | CNOT3 | Exon 15 Forward | CATCCTGAGCAGTACATCAGC | 50 nM | RT-PCR |
| 80 | CNOT3 | Exon 18 Reverse | CTCCAGGTAGCGGTACTCAA | 50 nM | RT-PCR |
| 81 | PRPF31 | Exon 2/3 Forward | GGGATAGTAAGATGTTTGCTGAG | 250 nM | qRT-PCR |
| 82 | PRPF31 | Exon 3/4 Reverse | GTCCCATCACTTCTGAAGCTTTGG | 250 nM | qRT-PCR |
| 83 | TBP | F | TCAGGCGTTCGGTGGATCGAGT | 500 nM | qRT-PCR |
| 84 | TBP | R | AGTGATGCTGGGCACTGCGGAGAA | 500 nM | qRT-PCR |
| 85 | GAPDH | F | ACAGTCAGCCGCATCTTCTT | 250 nM | qRT-PCR |
| 86 | GAPDH | R | AGGGGTCTACATGGCAACTG | 250 nM | qRT-PCR |
| 87 | CNOT3 | Exon 10 Forward | GACGTTCCACAGACAGTGAAG | | |
| 88 | CNOT3 | Exon 8 Reverse | GTGGTAGCGGTGCTTCTCGATG | | |
| 89 | CNOT3 | 3_5'UTR Forward | TATATTCGGGACTCGGGGG | | |

Figure 2A:
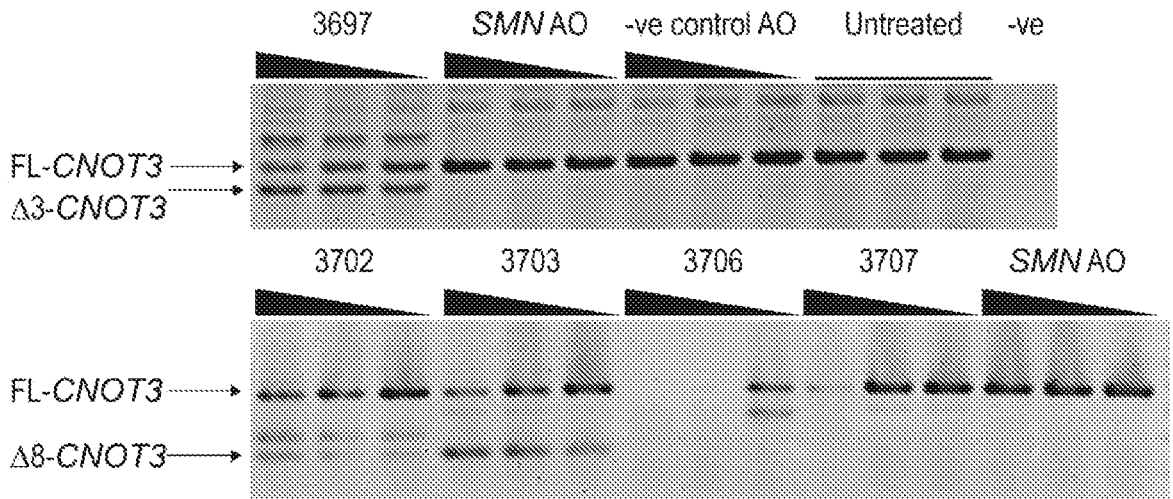
FIG. 2 is a gel image showing CNOT3 transcript products from RP11 patient fibroblasts 48 hr after 2'O-Methyl phosphorothioate AO transfection (50, 25 and 12.5 nM). Control AOs that target no known sequence (-ve control AO) were included for comparison.
Figure 2B:
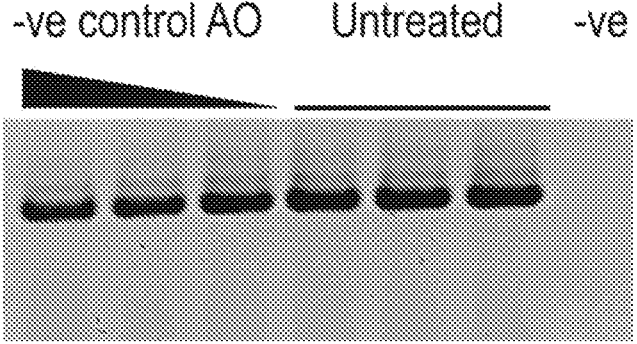

Sequencing of the induced (smaller) CNOT3 transcript products, predicted to result from induced exon skipping revealed that AOs 3697 and 3698 mediated exon 3 skipping, AO 3702 induced both partial and complete skipping of exon 8 and AO 3703 mediated dose dependant exon 8 skipping (data not shown). The AOs that mediated efficient CNOT3 exon 3, 8 or 9 skipping were then transfected into RP patient fibroblasts for 48 hrs and CNOT3 transcripts were analysed by RT-PCR (FIG. 2). CNOT3 exon skipping was evident 48 hr after transfection, with some reduction in the levels of full-length transcript product. Exon 3 was excluded by AO 3697, exon 8 was skipped by AOs 3702 and 3703 and exon 9 by AO 3706.

Previously, we have shown that the phosphorodiamidate morpholino (PMO) chemistry more effectively mediates splice modification than the same sequences synthesized as the 2'O-Methyl PS chemistry. Therefore, the most promising AO sequences for CNOT3 transcript knockdown will be synthesised as PMOs and transfected into normal fibroblasts uncomplexed, with a leash/lipoplex or via nucleofection (Nucleofector, Lonza). CNOT3-targeting AO sequence evaluation and optimisation is ongoing.

SH-SY5Y cells are often used as in vitro models of neuronal function and differentiation. They are adrenergic in phenotype but also express dopaminergic markers. AOs that modify CNOT3 transcripts in fibroblasts will be evaluated in differentiated SH-SY5Y cells for the ability to down-regulate CNOT3 and increase PRPF31 expression (transcript and protein).

Example 2

AO Mediated Terminal Intron Retention to Knock Down CNOT3

Antisense sequences were designed to target the terminal exon of CNOT3 in order to induce terminal intron retention and knock-down of CNOT3.

Figure 3:
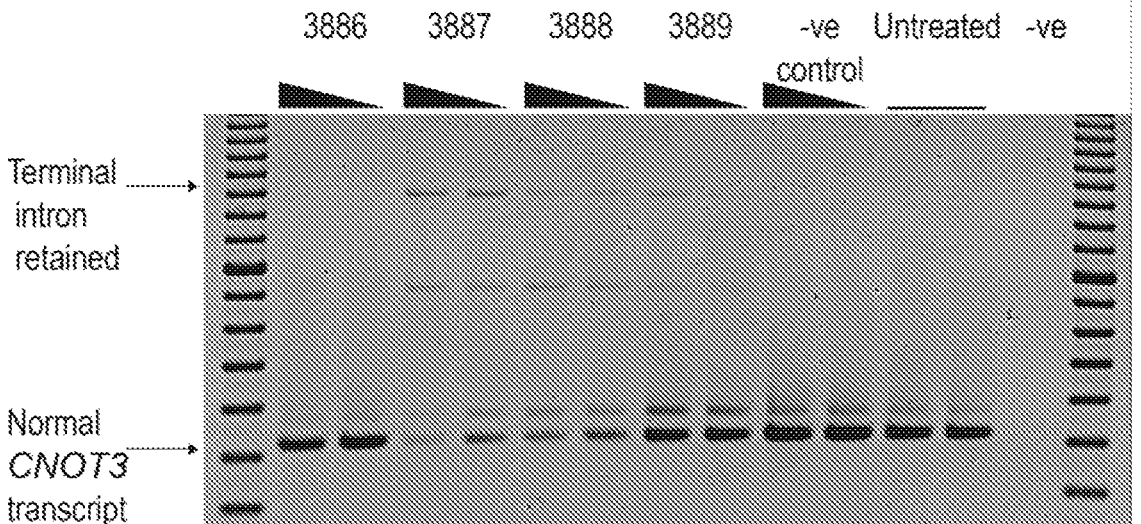
FIG. 3 is a gel image showing CNOT3 transcript products from fibroblasts 48 hr after transfection with 2'O-Methyl phosphorothioate AOs, designed to induce terminal intron retention, at concentrations of 50 and 25 nM.

2'O-Methyl AOs targeting the terminal exon of CNOT3 were transfected into adRP11 patient fibroblasts for 48 hr. RT-PCR analysis of the CNOT3 transcripts showed AOs 3887, 3888 and 3889 (Table 1) induced terminal intron retention and reduction in the level of full-length transcript product, in a dose dependent manner (FIG. 3).

Example 3

Recruitment and Review of Families with RP

Figure 4A:
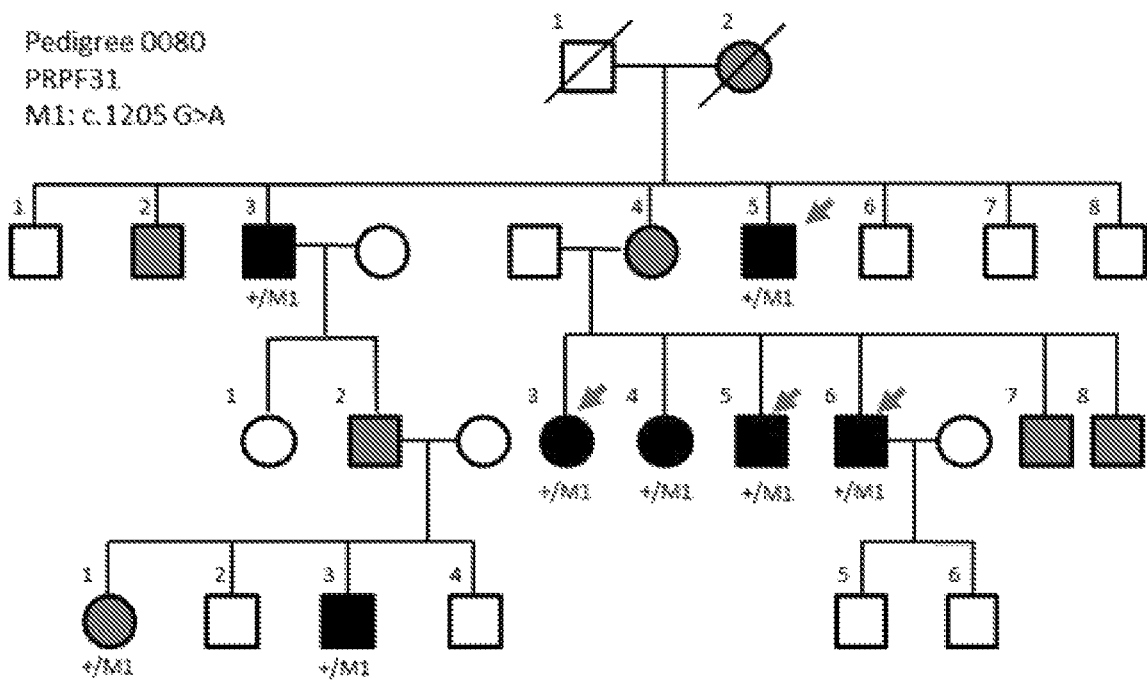
FIGS. 4A and 4B.
Figure 4B:
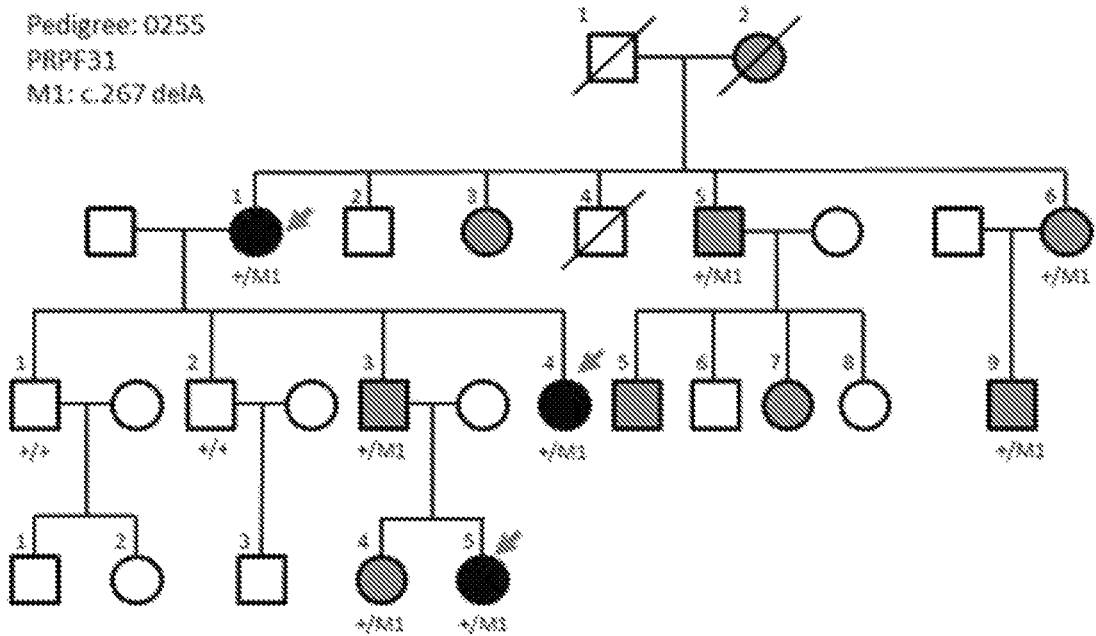

We have examined 3 generations of 2 families in WA (1 Caucasian and 1 Aboriginal) with PRPF31 mutations (FIG. 4). We have obtained dermal fibroblast from 7 patients and have started monitoring disease progression in 10 of 24 affected individuals in these families.

Example 4

Figure 5:
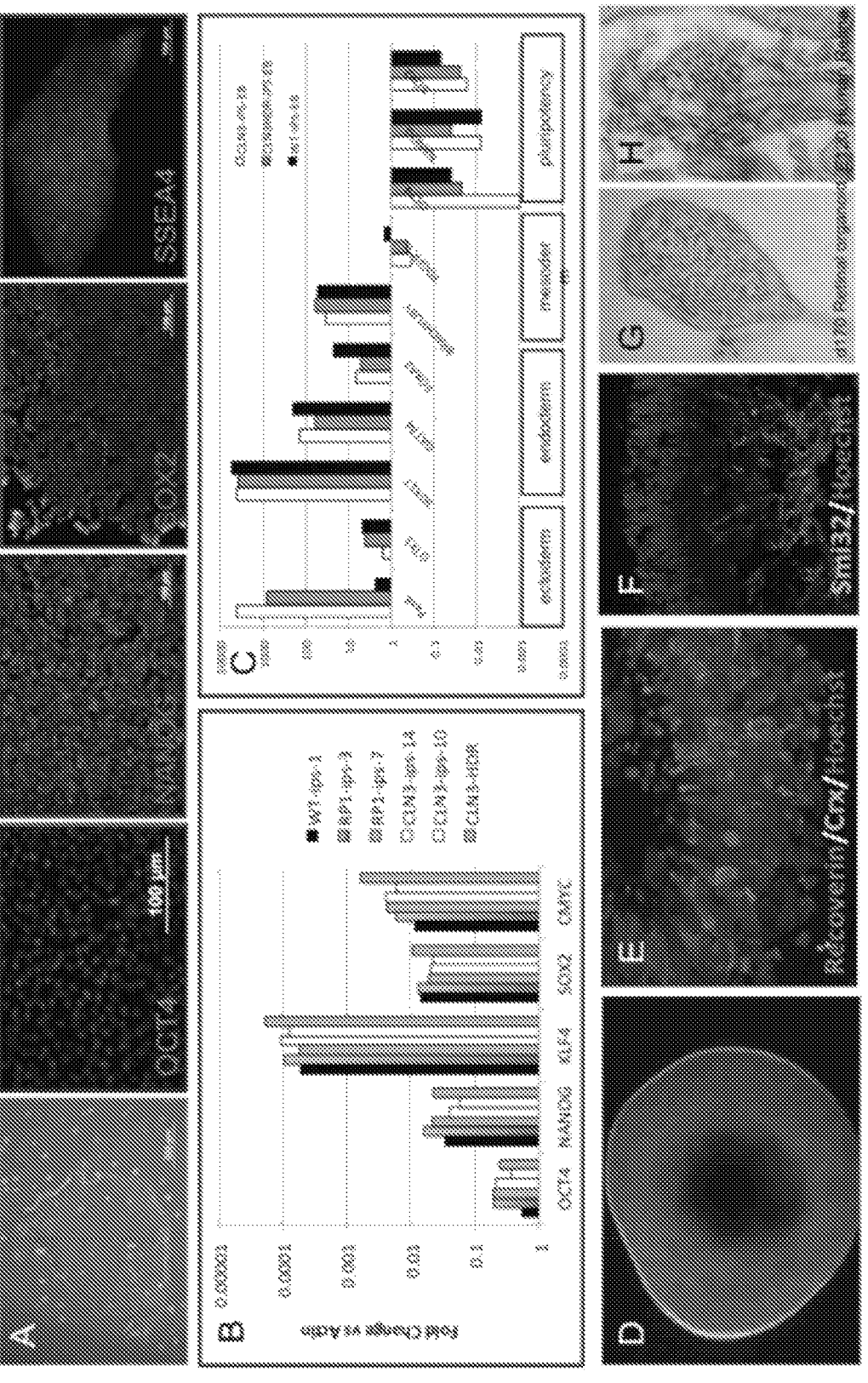
FIGS. 5A-H show skin fibroblasts from a patient with CLN3 mutation reprogrammed to pluripotency. Patient-iPSC (CLN3–/–) displayed typical iPSC morphology and expressed pluripotency markers, including OCT4, NANOG, SOX2 and SSEA4 (A). Comparison pluripotent gene expression in 6 iPSC lines by quantitative RT-PCR demonstrated similar expression patterns for all lines (B). Patient iPSC demonstrated trilineage differentiation potential. Patient iPSCs (CLN3-iPS-EB), gene corrected control iPSCs (CLN3HDR-IPS-EB) and control human iPSC (WT-IPS-EB, ThermoFisher) were differentiated as embryoid bodies for 2 weeks then screened for expression of markers of ectoderm (PAX6, OTX1), mesoderm (SOX17, GATA4, FOX2A) and endoderm (BRACHYURY, FDGFR) lineages, as well as pluripotency genes (OCT4, NANOG, SOX2) by quantitative RT-PCR (C). D-H: Retinal differentiation of iPSC. Retinal organoids displayed an optic cup-like morphology, surrounded by transparent, laminated retinal tissues (D) that contained an organized apical layer of recoverin expressing photoreceptors (E) as well as basally positioned Smi32 expressing retinal ganglion cells (F). Electron microscopy of photoreceptor outer segments in day 170 retinal organoids (G) demonstrated similar morphology to outer segments in the developing (E120) human retina (H).

Generate Induced Pluripotent Stem Cells from RP11 Patient and Control Fibroblasts and Assess Gene Expression as a Consequence of CNOT3 Knockdown Induced pluripotent stem cells will be generated from patient and control fibroblasts. Patient fibroblasts will be transfected with reprogramming episomes (ThermoFisher®) using the NEON® electroporation system. In a typical reprogramming experiment, 12-15 iPSC-like colonies are picked 3-4 weeks after transfection and subcultured for evaluation of pluripotent gene expression by immunostaining and RT-PCR analysis (FIG. 5A-C). Three clones will then be selected for additional testing, including gene expression profiling by TaqMan Arrays (Human Stem Cell Pluripotency Array, ThermoFisher) and virtual karyotyping by chromosomal G-band analyses with QuantiSNP analysis (AGRF).

To demonstrate tri-lineage differentiation potential, iPSC are cultured as embryoid bodies for 2-4 weeks and examined for expression of markers of ectoderm, mesoderm and endoderm differentiation, as well as the downregulation of pluripotency markers by RT-PCR (FIG. 5C). The iPSCs will be differentiated to retinal organoids using CIF's published protocol (Mellough et al., *Efficient stage-specific differentiation of human pluripotent stem cells toward retinal photoreceptor cells. Stem Cells,* 2012. 30 (4): p. 673-86.), (FIG. 5D-H).

The differentiated cells will be transfected with the lead CNOT3-targeting AO, synthesised as a morpholino compound, in triplicate for each analysis.

CNOT3, PRPF31 and other splicing factor transcripts will be analysed. CNOT3, PRPF31 and selected paraspeckle proteins and splicing factors will be assessed by Western blot and immunofluorescence to reflect the integrity of the splicing machinery and pathways.

Example 5

Dose Dependent Testing of AOs

Figure 6A:
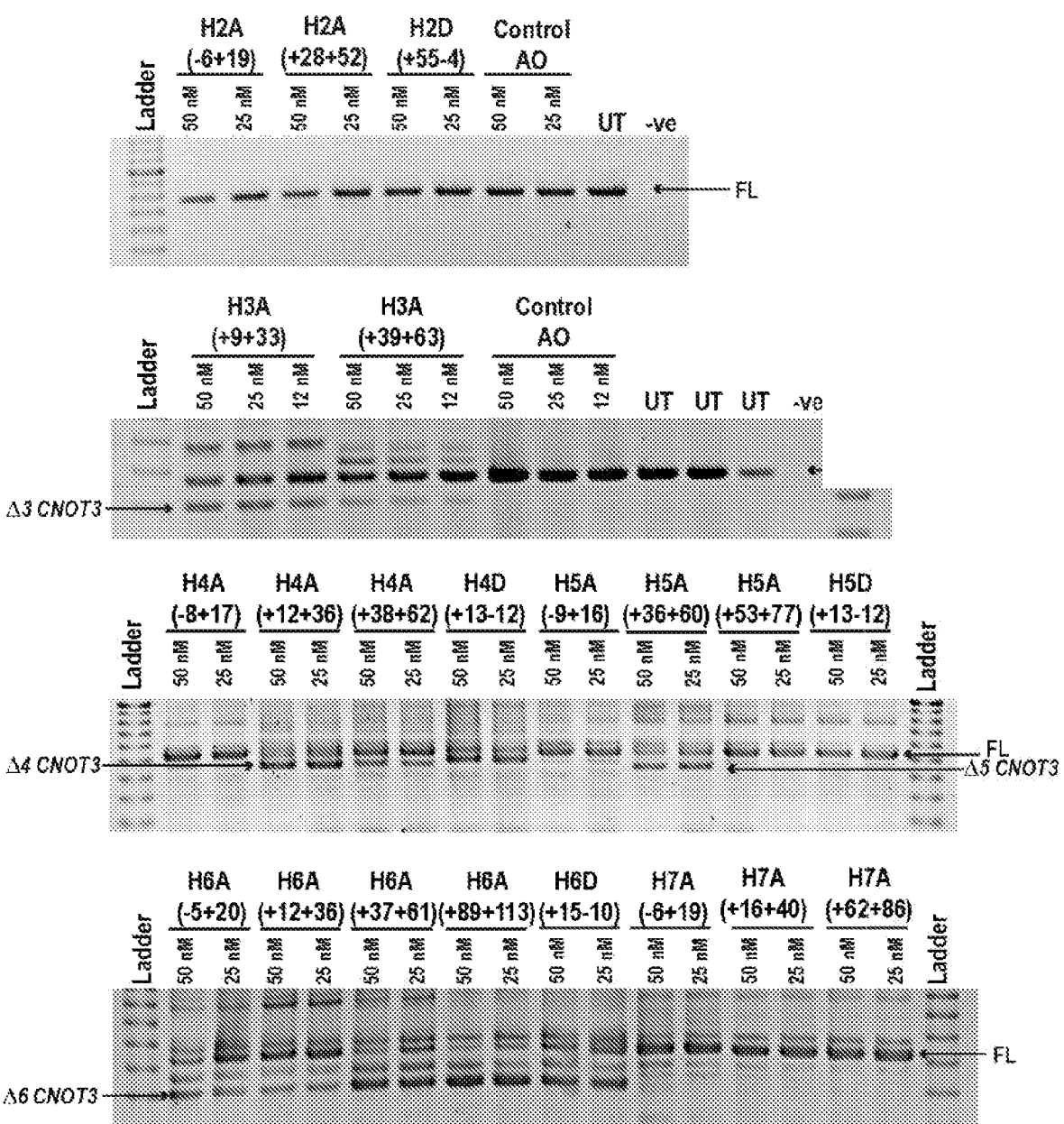
FIG. 6 shows screening of AO-induced CNOT3 exon skipping using 2'-O-Methyl chemistry on PS backbone. AOs are designed to target splice enhancer motifs of CNOT3 exons to mediate the exclusion of target exon(s) during pre-mRNA splicing in order to mediate knockdown of CNOT3 or disrupt protein function. Dermal fibroblasts were transfected for 48 hr with CNOT3 AOs (2'OMe-PS chemistry) targeting exons (as indicated). RT-PCR products were separated on 2% agarose gels.
Figure 6B:
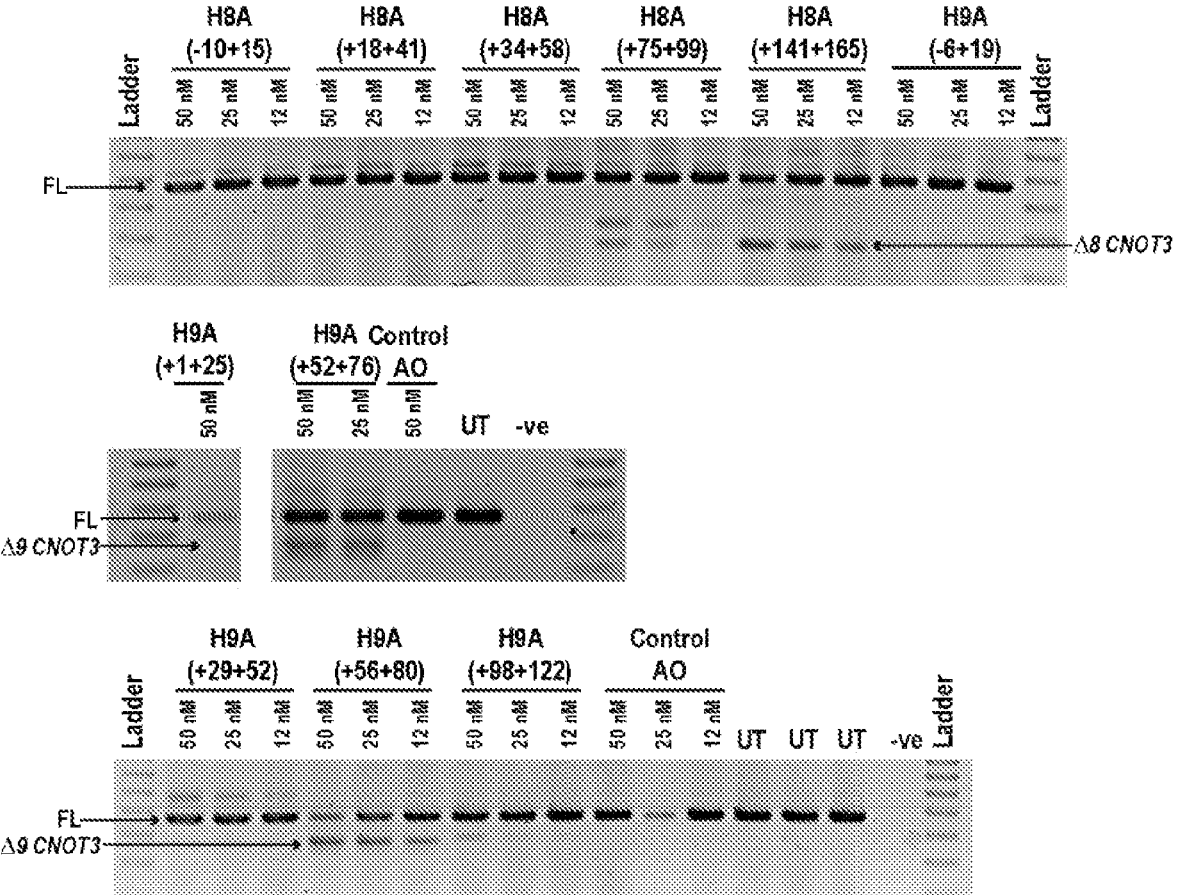
Figure 7A:
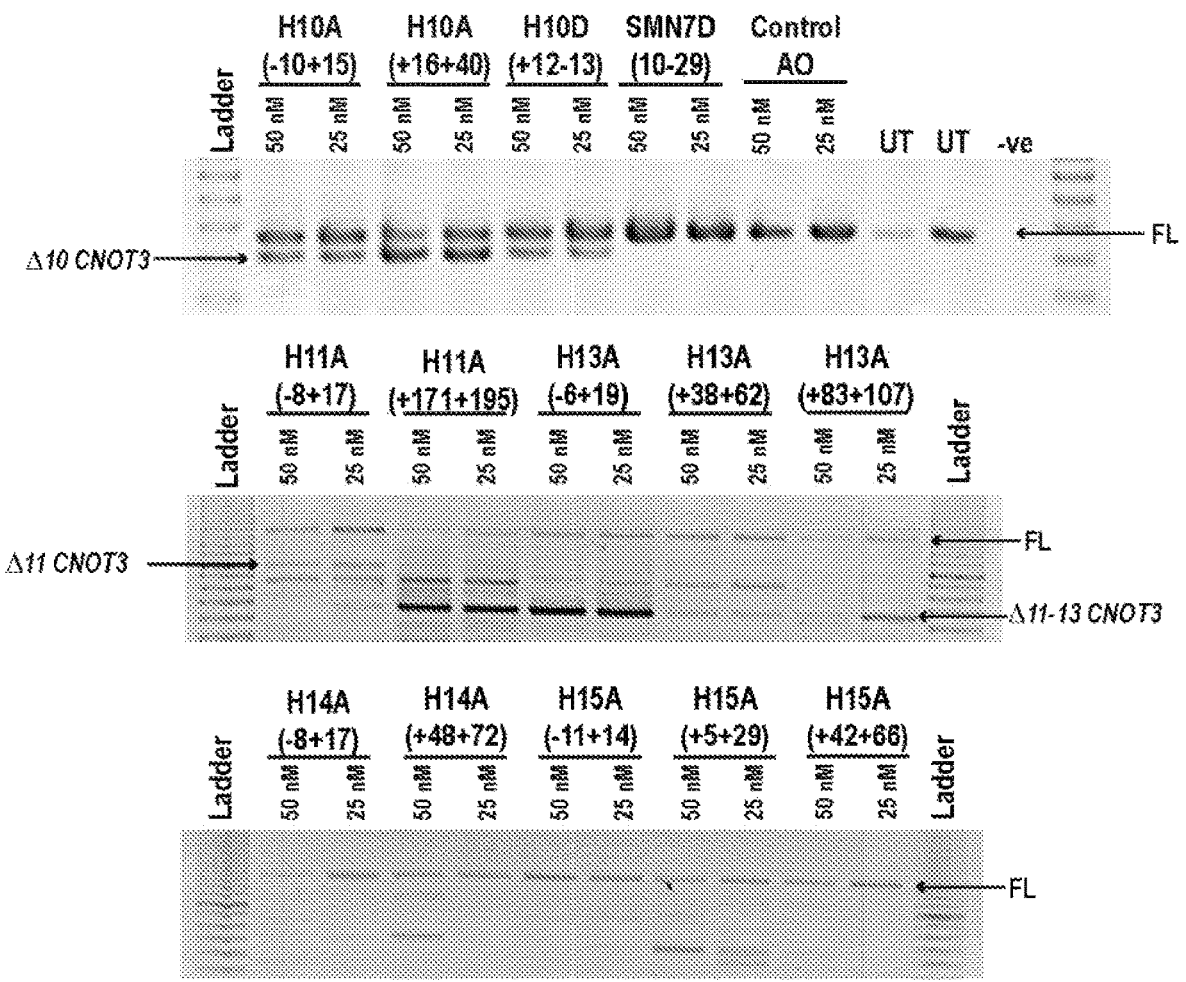
FIG. 7 shows screening of AO-induced CNOT3 exon skipping using 2'-O-Methyl chemistry on PS backbone. AOs
Figure 7B:
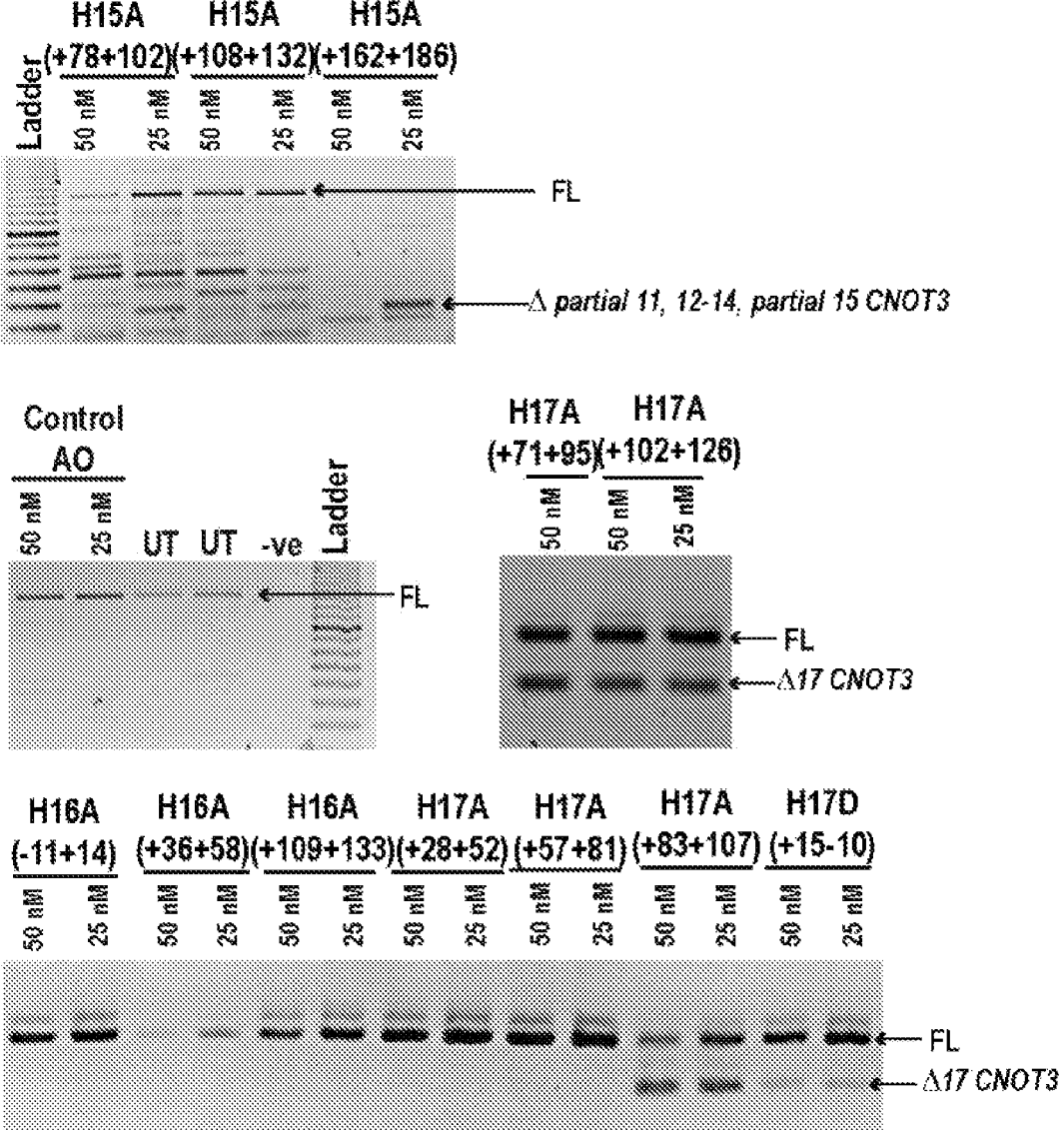

AO sequences were designed to skip selected exons from the CNOT3 messenger RNA and transfected as 2'O-Methyl phosphorothioate AOs into fibroblasts after complexing with cationic liposomes for efficient transfection. Skipping of the target exon results in a shortened messenger RNA RT-PCR product, identified by separation and staining of the products on a 2% agarose gel (FIGS. 6 and 7).

Preferred sequences show dose dependent target exon skipping. The lead sequences were then synthesized as phosphorodiamidate morpholino oligomers (PPMO) for testing by transfection into patient fibroblasts.

TABLE 3

RP11-causing mutations identified and respective number of patients with each confirmed mutation (information from Australian Inherited retinal disease register as of 2018).

| Mutation | Protein change | Phenotype | Number affected (state) |
|---|---|---|---|
| PRPF31.1205C > A | Ser402* | Dominant RP | 9 (WA) |
| PRPF31.267delA | Glu89Aspfs | Dominant RP | 8 (WA, Vic) |
| PRPF31.527 + 3A > G | N/A: SPLICE | Dominant RP | 3 (NSW) |
| PRPF31.319C > G | Leu107Val | Dominant RP | 1 (SA) |
| PRPF31.527 + 1G > T | N/A: SPLICE | Dominant RP | 1 (WA) |
| PRPF31.1289_1290insA | X | Dominant RP | 1 (SA) |

Figure 8A:
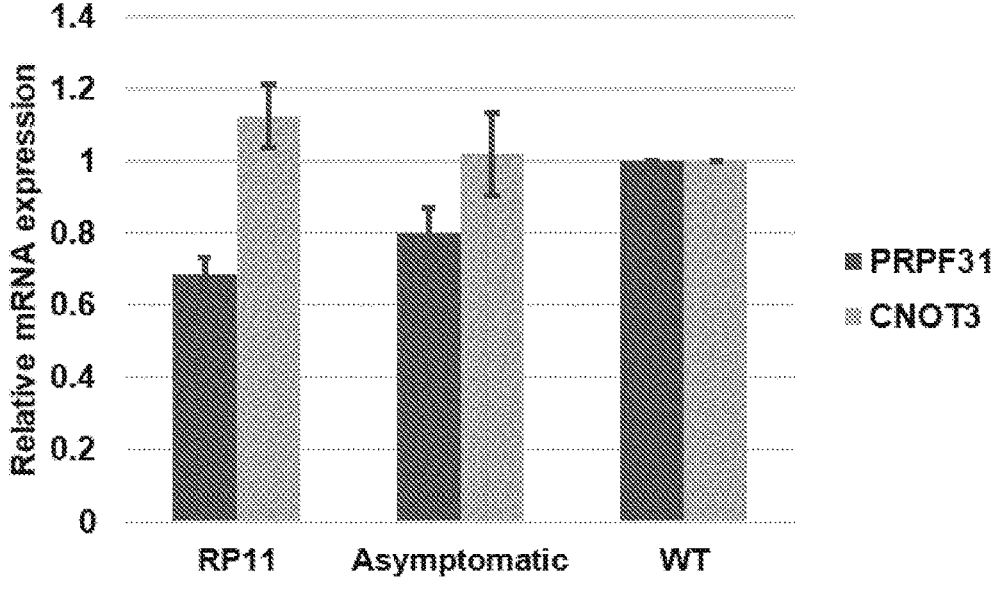
Figure 8B:
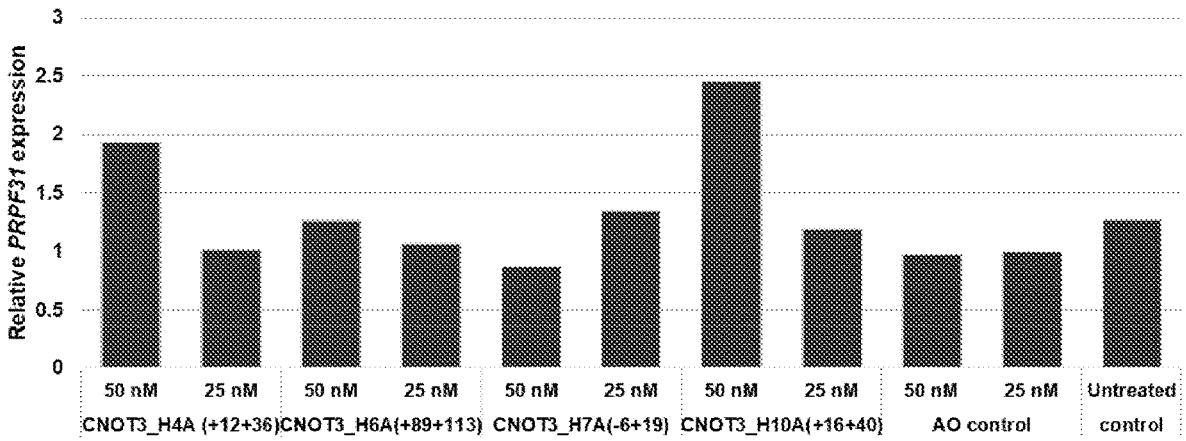
Figure 8C:
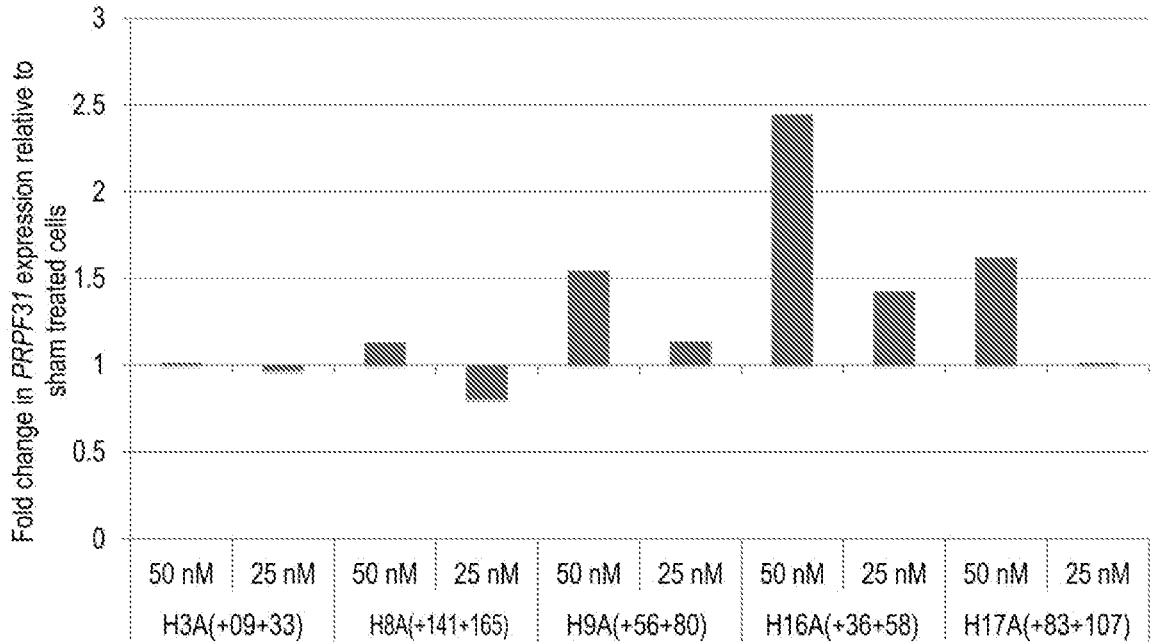

Patients with RP11 show PRPF31 levels of approximately 50% of those in the healthy population. Messenger RNAs for CNOT3 and PRPF31 were quantified by reverse transcription and quantitative PCR (qRT-PCR) in RP 11 family members and in a healthy control. FIG. 8a shows that higher CNOT3 expression correlates with reduced PRPF31 and clinical outcome in heterozygous PRPF31 mutation carriers. Skipping of target CNOT3 exons was assessed by qRT-PCR (FIG. 8b, 8c), and the PRPF31 expression after AO treatment is shown relative to that in cells treated with a control AO sequence (control AO 25 nM transfection value set to 1) that does not target any region of the healthy human genome (no effect expected—negative control). Data from untreated cells is included for comparison.

Patients with RP11 show PRPF31 levels of approximately 50% of those in the healthy population, whereas asymptomatic PRPF31 mutation carriers show levels of at least 70% of healthy levels, or higher. An increase of 1.5-fold of PRPF31 expression (e.g. CNOT3 exon 3 or 10 skipping, FIG. 8b and CNOT3 exons 9, 16, or 17 skipping, FIG. 8c) is expected to rescue splicing function in RP11 retinal pigment epithelium.

Example 6

Antisense Oligomer-Mediated CNOT3 Exon Skipping Upregulates PRPF31 Expression in RP11 Patient iPSC-Derived Retinal Pigment Epithelium (RPE) and Rescues Primary Cilia Length and Number ASO6 (SEQ ID NO: 64, CNOT3_H17A(+83+107), targeting CNOT3 exon 17) was synthesized as phosphorodiamidate morpholino oligomer (PMO) and transfected into RP11 iPSC-derived RPE by direct transfection using 5 uM ASO in culture media.

Immunocytochemistry was used for immunostaining of cilia and basal body in wildtype and RP11 RPE with or without antisense oligomer treatment.

Cilia Immunostaining Protocol

RPE cells on a chamber slide were fixed using ice cold acetone-methanol (1:1) for 4 minutes then air dried. Cells were blocked for 30 minutes in 10% filtered goat serum in PBS. For basal body staining, cells were incubated with mouse anti-pericentrin antibody (1:100) for 1 hr at room temperature. Primary antibody was detected using AlexaFluoro488 anti-mouse (1:400). For cilia staining, cells were incubated with rabbit anti-ARL13B antibody (1:500) and incubated overnight at 4° C. Second primary antibody was detected using AlexaFluoro568 anti-rabbit (1:400) for 1 hr at room temperature and counterstained with Hoechst for nuclei detection (dilution 1:125). A coverslip was mounted onto a slide using Prolong Gold anti-fade media.

Confocal Analysis and Quantification

Primary cilia of RPE were assessed to evaluate PRPF31 function using confocal microscopy. Approximately 300 RPE cells/sample were measured for cilia length using NIS-Elements Imaging Software.

---

The invention claimed is:

1. An isolated or purified antisense oligomer for modifying pre-mRNA splicing in the CNOT3 gene transcript or part thereof, wherein the sequence of the antisense oligomer is selected from the list consisting of: SEQ ID NOs: 4, 7-9, 11, 14-18, 26, 27, 30-35, 39, 40, 44-48, 53-57, 59, 60, 64, 67, 69, 70, and 72-74; wherein the antisense oligomer comprises one or more nucleotide positions having an alternative chemistry or a modification selected from the group consisting of: (i) a modified backbone structure; (ii) modified sugar moieties; (iii) resistance to RNase H; and (iv) oligomeric mimetic chemistry.

2. The antisense oligomer of claim 1, wherein the sequence of the antisense oligomer is selected from the group consisting of: SEQ ID NOs: 4, 7, 9, 11, 15, 16-18, 27, 30, 34, 35 and 64.

3. The antisense oligomer of claim 1, wherein the sequence of the antisense oligomer is selected from the group consisting of: SEQ ID NOs: 4, 7, 27, 30, 34, and 64.

4. The antisense oligomer of claim 1, wherein the antisense oligomer further comprises: (i) a chemically conjugated moiety; or (ii) a cell penetrating peptide.

5. The antisense oligomer of claim 1, wherein the antisense oligomer is a phosphorodiamidate morpholino oligomer.

6. The antisense oligomer of claim 1 wherein when any uracil (U) is present in the nucleotide sequence, the uracil (U) is replaced by a thymine (T).

7. The antisense oligomer of claim 1 that operates to induce skipping of one or more of the exons of the CNOT3 gene transcript or part thereof.

8. The antisense oligomer of claim 1 that results in the expression of a PRPF31 protein between 1.5 and 5 fold higher than the expression of the PRPF31 protein in subjects with symptomatic PRPF31 mutations.

9. A pharmaceutical composition comprising:

a) a therapeutically effective amount of one or more antisense oligomers according to claim 1, and b) one or more pharmaceutically acceptable carriers and/or diluents.

10. A method for treating retinitis pigmentosa, comprising the step of administering to the patient a therapeutically effective amount of one or more antisense oligomers or pharmaceutical composition comprising one or more antisense oligomers, wherein the sequence of the antisense oligomer is selected from the group consisting of: SEQ ID NOs: 4, 7-9, 11, 14-18, 26, 27, 30-35, 39, 40, 44-48, 53-57, 59, 60, 64, 67, 69, 70, and 72-74.

11. The method of claim 10 wherein the patient is a human.

12. The method of claim 10 that results in the expression of a PRPF31 protein between 1.5 and 5 fold higher than the expression of the PRPF31 protein in subjects with symptomatic PRPF31 mutations.

13. The method of claim 10, wherein the sequence of the antisense oligomer is selected from the group consisting of: SEQ ID NOs: 4, 7, 9, 11, 15, 16-18, 27, 30, 34, 35 and 64.

14. The method of claim 10, wherein the sequence of the antisense oligomer is selected from the group consisting of SEQ ID NOs: 4, 7, 27, 30, 34 and 64.

* * * * *